US007811814B2

(12) United States Patent
Bohn et al.

(10) Patent No.: US 7,811,814 B2
(45) Date of Patent: Oct. 12, 2010

(54) TETRACYCLINE-REGULATED ADENO-ASSOCIATED VIRAL (AAV) VECTORS FOR GENE DELIVERY TO THE NERVOUS SYSTEM

(75) Inventors: Martha C. Bohn, Chicago, IL (US); Lixin Jiang, Guangdong (CN); Neva C. West, Chicago, IL (US); Elio F. Vanin, Chicago, IL (US)

(73) Assignee: Children's Memorial Hospital, Chicago, IL (US)

( * ) Notice: Subject to any disclaimer, the term of this patent is extended or adjusted under 35 U.S.C. 154(b) by 0 days.

(21) Appl. No.: 12/211,409

(22) Filed: Sep. 16, 2008

(65) Prior Publication Data

US 2009/0149409 A1 Jun. 11, 2009

Related U.S. Application Data

(60) Division of application No. 11/600,009, filed on Nov. 15, 2006, now Pat. No. 7,456,015, which is a continuation-in-part of application No. PCT/US2005/015612, filed on May 5, 2005.

(60) Provisional application No. 60/572,460, filed on May 18, 2004, provisional application No. 60/775,747, filed on Feb. 22, 2006.

(51) Int. Cl.
  *C12N 15/00* (2006.01)
  *C12N 15/09* (2006.01)
  *A61K 31/00* (2006.01)
  *A61K 31/70* (2006.01)
  *A61K 31/711* (2006.01)

(52) U.S. Cl. .................................... 435/320.1; 514/44

(58) Field of Classification Search .............. 435/320.1; 514/44
See application file for complete search history.

(56) References Cited

U.S. PATENT DOCUMENTS

| 5,770,414 | A | 6/1998 | Gage et al. |
|---|---|---|---|
| 5,965,440 | A * | 10/1999 | Reeves ........................ 435/456 |
| 6,180,613 | B1 | 1/2001 | Kaplitt et al. |
| 6,503,888 | B1 | 1/2003 | Kaplitt et al. |
| 6,544,780 | B1 * | 4/2003 | Wang ....................... 435/320.1 |
| 6,610,290 | B2 | 8/2003 | Podsakoff et al. |
| 6,875,568 | B2 | 4/2005 | Nisson et al. |

FOREIGN PATENT DOCUMENTS

WO   WO 2005/116224 A2   12/2005

OTHER PUBLICATIONS

Baron, U. et al.; "Tet Repressor-Based System for Regulated Gene Expression in Eukaryotic Cells: Principles and Advances;" Methods in Enzymology, vol. 327; 2000; pp. 401-421.

Baron, U. et al.; "Tetracycline-controlled transcription in eukaryotes : novel transactivators with graded transactivation potential;" Nucleic Acids Research; 1997; vol. 25, No. 14; pp. 2723-2729.

Blesch, A. et al.; "Neurite Outgrowth Can Be Modulated In Vitro Using a Tetracycline-Repressible Gene Therapy Vector Expressing Human Nerve Growth Factor;" Journal of Neuroscience Research 59:402-409 (2000).

Connor, B. et al.; "Differential effects of glial cell line-derived neurotrophic factor (GDNF) in the striatum and substantia nigra of the aged Parkinsonian rat;" Gene Therapy (1999) 6; 1936-1951; 1999.

Corti, O. et al.; "A single adenovirus vector mediates doxycycline-controlled expression of tyrosine hydroxylase in brain grafts of human neural progenitors;" Nature Biotechnology, vol. 17; Apr. 1999; pp. 349-354.

Fitzsimons, H.L. et al.; "Insulators coupled to a minimal bidirectional tet cassette for tight regulation of rAAV-mediated gene transfer in the mammalian brain;" Gene Therapy (2001) 8, 1675-1691.

Gossen, M. et al.; "Tight control of gene expression in mammalian cells by tetracycline-responsive promoters;" Proc. Natl. Acad. Sci. USA; vol. 89; pp. 5547-5551; Jun. 1992; Cell Biology.

Jiang, L. et al.; "Quantitation of Transgene Expression from Self-regulating rAAV Vectors by Flow Cytometry;" American Society of Gene Therapy; Molecular Therapy vol. 5, May 2002, Part 2 of 2 Parts; © The American Society of Gene Therapy, S138; Abstract.

Jiang, L. et al.; "Quantitation of Transgene Expression from Self-regulating rAAV Vectors by Flow Cytometry;" Poster presented at American Society of Gene Therapy meeting on Jun. 6, 2002.

Jiang, L. et al.; "Self regulating rAAV vectors using a tetracycline ( TET )—off promoter are tightly regulated in vitro and in vivo;" Society for Neuroscience Abstract Viewer and Itinerary Planner; vol. 2003, 2003, pp. Abstract No. 79.19; $33^{rd}$ Annual Meeting of the Society of Neuroscience: New Orleans, LA, U.S.A.

Jiang, L. et al.; "Tight Regulation from a rAAV Vector as Demonstrated by Flow Cytometry and Quantitative RT-PCR;" Society for Neuroscience Abstract Viewer and Itinerary Planner; vol. 2002, 2002, pp. Abstract No. 902.4; $32^{nd}$ Annual Meeting of the Society for Neuroscience; Orlando, Florida, U.S.A.; Nov. 2-7, 2002.

Jiang, L. et al.; "Tight Regulation from a single tet-off rAAV vector as demonstrated by flow cytometry and quantitative real-time PCR;" Gene Therapy (2004) 11; pp. 1057-1067.

Kozak, M.; "Structural Features in Eudaryotic mRNAs That Modulate the Initiation of Translation;" The Journal of Biological Chemistry, vol. 266, No. 30, Issue of Oct. 25; pp. 19867-19870; 1991.

(Continued)

*Primary Examiner*—Kevin K. Hill
(74) *Attorney, Agent, or Firm*—Brinks Hofer Gilson & Lione

(57) ABSTRACT

A vector and a method are provided for delivering a nucleic acid to a nervous system cell. The vector includes a first nucleic acid, a second nucleic acid, inverted terminal repeats of adeno-associated virus, and a tetracycline-off regulatable promoter system that includes a first promoter operably linked to the first nucleic acid and a second promoter operably linked to the second nucleic acid. The promoters drive expression in opposite directions and away from the inverted terminal repeats. The method includes providing a recombinant adeno-associated viral (rAAV) vector and administering the vector to a nervous system cell. Expression of a product from the first nucleic acid is regulatable by the promoter system.

13 Claims, 13 Drawing Sheets

OTHER PUBLICATIONS

Sànchez-Pernaute, R. et al.; "Functional Effect of Adeno-associated Virus Mediated Gene Transfer of Aromatic $_L$-Amino Acid Decarboxylase into the Striatum of 6-OHDA-Lesioned Rats;" Molecular Therapy, vol. 4, Issue 4; Oct. 2001; pp. 324-330 (Abstract).

Urlinger, S. et al.; "Exploring the sequence space for tetracycline-dependent transcriptional activators: Novel mutations yield expanded range and sensitivity;" Proc. Natl. Acad. Sci. USA, 97: 7963-7968, 2000.

International Search Report dated Dec. 7, 2005 for International Application No. PCT/US2005/015612.

Berns and Bohenzky, "Adeno-Associated Viruses: An Update"; *Advances in Virus Research* (Academic Press, Inc.) 32:243-307, 1987.

Bohl et al., "Modulation of Erythropoietin Delivery from Engineered Muscles in Mice"; *Hum. Gene Ther.*, 8:195-204, Jan. 1997.

Chenaud, P. et al.; "Optimal Design of a Single Recombinant Adeno-associated Virus Derived from Serotypes 1 and 2 to Achieve More Tightly Regulated Transgene Expression from Nonhuman Primate Muscle;" Mol. Ther. Mar. 2004; 9(3):410-8.

Choi-Lundberg, D.L. et al.; "Dopaminergic Neurons Protected from Degeneration by GDNF Gene Therapy"; Science, 275, 838-841, Feb. 7, 1997.

Clark et al., "Highly Purified Recombinant Adeno-Associated Virus Vectors Are Biologically Active and Free of Detectable Helper and Wild-Type Viruses;" Hum. Gene Ther., 10: 1031-1039, Apr. 1999.

Eberling, J.L.; "In Vivo PET Imaging of Gene Expression in Parkinsonian Monkeys"; *Mol. Ther.*, 8:873-875, Dec. 2003.

Flotte et al., "Expressions of the Cystic Fibrosis Transmembrane Conductance Regulator from a Novel Adeno-associated Virus Promoter"; J. Biol. Chem., 268: 3781-3790, Feb. 1993.

Gossen, M. et al.; "Tight control of gene expression in mammalian cells by tetracycline-responsive promoters;" Proc. Natl. Acad. Sci. USA; vol. 89; pp. 5547-5551; Jun. 1992; Cell Biology.

Grimm et al., "Novel Tools for Production and Purification of Recombinant Adenoassociated Virus Vectors"; *Hum. Gene Ther.*, 9: 2745-2760, Dec. 1998.

Hasan et al., "Long-Term, Noninvasive Imaging of Regulated Gene Expression in Living Mice"; Genesis, 29: 116-122, 2001.

Kaludov et al., "Scalable Purification of Adeno-Associated Virus Type 2, 4, or 5 Using Ion-Exchange Chromatography"; Hum. Gene Ther., 13: 1235-1243, Jul. 2002.

Kozak, M., "Point Mutations Define a Sequence Flanking the AUG Initiator Codon That Modulates Translation by Eukaryotic Ribosomes"; Cell, 44(2):283-92, Jan. 1986.

Kozak, M.; "An analysis of 5'-noncoding sequences from 699 vertebrate messenger RNAs"; Nucleic Acids Res., Oct. 26;15(20):8125-48, 1987.

Kozak, M.; "Structural Features in Eudaryotic mRNAs That Modulate the Initiation of Translation;" The Journal of Biological Chemistry, vol. 266, No. 30, Issue of Oct. 25; pp. 19867-19870; 1991.

Kozlowski et al., "Quantitative Analysis of Transgene Protein, mRNA, and Vector DNA Following Injection of an Adenoviral Vector Harboring Glial Cell Line-Derived Neurotrophic Factor into the Primate Caudate Nucleus"; Mol. Ther., 3: 256-261, Feb. 2001.

Lo et al., "Adeno-Associated Virus-Mediated Gene Transfer to the Brain: Duration and Modulation of Expression"; Hum. Gene Ther., 10: 201-213, Jan. 1999.

Muzyczka, "Use of Adeno-Associated Virus as a General Transduction Vector for Mammalian Cells"; *Curr Topics Microbiol. Immunol.* 158:97, 1992.

Peel et al., "Adeno-associated virus vectors: activity and applications in the CNS"; J. Neurosci. Methods, 98:95-104, 2000.

Veldwijk et al., "Development and Optimization of a Real-Time Quantitative PCR-Based Method for the Titration of AAV-2 Vector Stocks"; Mol. Ther., 6: 272-278, Aug. 2002.

Xiao et al., "Production of High-Titer Recombinant Adeno-Associated Virus Vectors in the Absence of Helper Adenovirus"; J. Virol., 72: 2224-2232, Mar. 1998.

Xu et al., "Quantitative comparison of expression with adeno-associated virus (AAV-2) brain-specific gene cassettes"; Gene Therapy, 5: 1323-1332, 2001.

Zolotukhin et al., "Recombinant adeno-associated virus purification using novel methods improves infectious titer and field"; Gene Therapy 6: 973-985, 1999.

\* cited by examiner ly the production of large-scale high titer rAAV free of contaminating helper virus (Grimm et al., *Hum. Gene Ther.,* 9: 2745-2760, 1998; Xiao et al., *J. Virol.,* 72: 2224-2232, 1998; Clark et al., *Hum. Gene Ther.,* 10: 1031-1039, 1999; Zolotukhin et al., *Gene Therapy* 6: 973-985, 1999).

TETRACYCLINE-REGULATED ADENO-ASSOCIATED VIRAL (AAV) VECTORS FOR GENE DELIVERY TO THE NERVOUS SYSTEM

This application is a divisional application of U.S. application Ser. No. 11/600,009, filed Nov. 15, 2006, now U.S. Pat. No. 7,456,015 which claims the benefit under 35 U.S.C. §371 of International Application No. PCT/US2005/015612, filed May 5, 2005, which claims the benefit of U.S. Provisional Application No. 60/572,460, filed May 18, 2004. U.S. application Ser. No. 11/600,009 also claims the benefit of U.S. Provisional Application No. 60/775,747, filed Feb. 22, 2006. These references are incorporated herein in their entirety.

FEDERALLY SPONSORED RESEARCH OR DEVELOPMENT

This invention was made with support under Grant Nos. NS31957 and NS045309 from the National Institute of Neurological Disorders and Stroke. The government may have certain rights in this invention.

FIELD OF THE INVENTION

The present invention generally relates to recombinant adeno-associated viral (rAAV) vectors for gene delivery and more specifically relates to tetracycline-regulatable rAAV vectors for gene delivery to the nervous system.

BACKGROUND

Gene delivery is a promising method for the treatment of acquired and inherited diseases. Gene delivery to the nervous system presents several problems including the quiescent nature of neuronal cells and the blood-brain barrier for delivery of genes to the brain. A majority of gene therapy trials have used retroviral-mediated gene transfer, which typically is used for gene delivery into dividing somatic cell populations and requires cell division for integration and expression. The requirement for cell division in retroviral gene therapy makes the use of retroviruses for gene delivery to the nervous system unlikely.

More recently, other types of viral vectors have been used, including recombinant vectors based on AAV particles. The viral genome of AAV consists of a 4.7 kb single-stranded DNA molecule, which is composed of two 145-base inverted terminal repeats (ITRs) flanking two open reading frames, Rep and Cap. In vectors designed for gene delivery, the Rep and Cap open reading frames are deleted and the only viral sequences in the rAAV vectors are the ITRs. AAV is a helper-dependent DNA parvovirus which belongs to the genus *Dependovirus.* AAV has a wide host range and is able to replicate in cells from any species so long as there is also a successful infection of such cells with a suitable helper virus. AAV has not been associated with any human or animal disease. For a review of AAV, see, e.g., Berns and Bohenzky, *Advances in Virus Research* (Academic Press, Inc.) 32:243-307, 1987.

Recombinant adeno-associated viral (rAAV) vectors have several properties that make them one of the most promising vehicles for gene delivery to the central nervous system (CNS). rAAV vectors have been reported to infect and transduce both dividing and non-dividing cells, including neurons with minimal cellular toxicity or host immune response (Peel et al., *J. Neurosci. Methods,* 98:95-104, 2000). In the central nervous system (CNS), significant long-term transduction of neurons by rAAV has been observed for up to 1 year (Xu et al., *Gene Therapy,* 5: 1323-1332, 2001; Lo et al., *Hum. Gene Ther.,* 10: 201-213, 1999).

Previously, use of rAAV was hampered by the lack of methods for producing high titer vectors that were not contaminated with helper viruses, such as adenovirus or herpes simplex virus. Recent developments in helper virus-free packing systems and a new purification protocol have made possible the production of large-scale high titer rAAV free of contaminating helper virus (Grimm et al., *Hum. Gene Ther.,* 9: 2745-2760, 1998; Xiao et al., *J. Virol.,* 72: 2224-2232, 1998; Clark et al., *Hum. Gene Ther.,* 10: 1031-1039, 1999; Zolotukhin et al., *Gene Therapy* 6: 973-985, 1999).

An important consideration in applying gene delivery to the CNS is the effect on the patient that may result from chronic, continuous expression in the nervous system of a biologically active molecule that could affect cells in addition to the target cells. This consideration is particularly relevant for neurotrophic factors since these are secreted molecules whose receptors are often widespread in the CNS. Therefore, an ideal vector for in vivo gene therapy of a nervous system disorder should include not only the ability to effectively and safely transduce the therapeutic gene into the nervous system, but also the ability to temporally regulate gene expression.

Regulatable promoter systems have been studied for transgene regulation in mammalian cells. Examples of promoter systems that have been developed for regulatable gene expression systems include a tetracycline-responsive (tet), a RU-486-inducible promoter, an ecdysone-inducible promoter, a rapamycin-inducible promoter, and a metallothionein promoter. Previously, gene delivery vectors have been used for delivery of therapeutic genes without regulatable elements.

The tet response element-based system is well characterized and was first described by Gossen and Bujuard (*Proc. Natl. Acad. Sci. USA,* 89:5547-5551, 1992). The tet system includes several advantages. The elements required for control of the tet system are derived from a prokaryotic organism, and thus, there is no endogenous expression of these control elements in mammalian cells. In addition, a preferred effector doxycycline (dox), a tet derivative, is an FDA approved drug that can regulate the transgene expression at very low concentrations without producing detectable side effects (Corti et al., *Nat. Biotechnol,* 17: 349-354, 1999; Hasan et al., *Genesis,* 29: 116-122, 2001). Activation of the tet-regulated system by dox is dose-dependent and gene expression can be controlled over a narrow window of dox concentrations (Urlinger et al., *Proc. Natl. Acad. Sci. USA,* 97: 7963-7969, 2000). The genes required for the tet system are small compared to elements required for other systems, which is advantageous given the limited insert size of approximately 4.5 kb, for rAAV vectors (Baron et al., *Methods Enzymol.,* 327: 401-421, 2000).

The tet inducible system includes two components, the tet-controlled transactivator protein (tTA), and the tet-regulated element (TRE). The tTA is a fusion protein of the tet repressor DNA binding domain of *Escherichia coli* (TetR) and the C-terminal transcriptional activator domain of the VP16 protein from herpes simplex virus. The TRE region includes seven copies of the tetracycline resistance operator binding sites and a minimal cytomegalovirus (CMV) promoter region that contains the TATA box and transcription start sites. In the absence of tet or dox, tTA can bind a tetracycline operator (tetO) sequence located in front of the minimal promoter and stimulate transcription of the transgene. Dox prevents this binding and consequently abolishes transcription because the minimal promoter by itself is inactive. This tet-off system has also been modified to make a tet-on system. When the tTA is replaced by a mutated transactivator, rtTA, the promoter regulation by the transactivator is reversed so that transgene expression occurs in the presence of dox and is shut off in the absence of dox. (Gossen et al., *Proc. Natl. Acad. Sci. USA*, 89:5547-5551, 1992; Urlinger et al., *Proc. Natl. Acad. Sci. USA*, 97: 7963-7969, 2000; Baron et al., *Methods Enzymol.*, 327: 401-421, 2000).

The tet-off and tet-on systems have been studied in the context of various viral vectors. In some cases, the two components of the tet system have been cloned into separate viruses, which requires coinfection of the target cells by both viruses to obtain regulatable transgene expression (see, for example, Bohl et al., *Hum. Gene Ther.*, 8:195-204, 1997). Another strategy is to combine both components into one self-regulating virus so that target cells only need to be infected by one virus to allow regulatable expression. (see, for example, Corti et al., *Nat. Biotechnol.*, 17: 349-354, 1999).

However, the limited insert size of in rAAV for foreign genes makes it difficult to design a tet-regulatable vector with an insulator region between the two tet expression cassettes to minimize promoter activity originating from the ITRs which are necessary for rAAV packaging (Fitzsimons et al., *Gene Therapy*, 8: 1675-1681, 2001; Flotte et al., *J. Biol. Chem.*, 268: 3781-3790, 1993). This limitation may result in leaky regulation of gene expression in the context of vector backbone.

A need exists for a tightly regulatable gene delivery vector for delivery of therapeutic genes to the nervous system.

BRIEF SUMMARY

In one aspect of the present invention, a regulatable recombinant adeno-associated viral vector is provided. The vector includes a first nucleic acid for providing a therapeutic effect on a nervous system disorder when a product is produced from the first nucleic acid and a second nucleic acid encoding a tetracycline-controlled transactivator. The vector further includes inverted terminal repeats from adeno-associated virus and a tetracycline-off regulatable promoter system having a first promoter operably linked to the first nucleic acid and a second promoter operably linked to a second nucleic acid. The first and second promoters drive expression in opposite directions, towards each other and away from the inverted terminal repeats.

In another aspect of the present invention, a method of delivering a first nucleic acid to a nervous system cell in a patient having a nervous system disorder is provided. The method includes providing a recombinant adeno-associated viral (rAAV) vector and administering the vector to a nervous system cell. The vector includes the first nucleic acid encoding a protein that provides a therapeutic effect on the nervous system disorder, a second nucleic acid encoding a tetracycline-controlled transactivator, inverted terminal repeats of adeno-associated virus, and a tetracycline regulatable promoter system that includes a first promoter operably linked to the first nucleic acid and a second promoter operably linked to the second nucleic acid. Expression of a product from the first nucleic acid is regulatable by the promoter system.

In yet another aspect of the present invention, a method of making recombinant AAV virions is provided. The method includes providing a recombinant adeno-associated viral vector (rAAV) and an AAV derived helper plasmid to producer cells, providing a helper virus; and culturing the producer cells to make the virions. The rAAV vector includes the first nucleic acid, a second nucleic acid encoding a tetracycline-controlled transactivator; inverted terminal repeats of AAV; and a tetracycline-off regulatable promoter system comprising a first promoter operably linked to the first nucleic acid and a second promoter operably linked to the second nucleic acid, wherein the first and second promoters drive expression in opposite directions in the vector, towards each other and away from the inverted terminal repeats.

Advantages of the present invention will become more apparent to those skilled in the art from the following description of the preferred embodiments of the present invention that have been shown and described by way of illustration. As will be realized, the invention is capable of other and different embodiments, and its details are capable of modification in various respects. Accordingly, the drawings and description are to be regarded as illustrative in nature and not as restrictive.

DETAILED DESCRIPTION OF THE DRAWINGS AND THE PRESENTLY PREFERRED EMBODIMENTS

Figure 1:
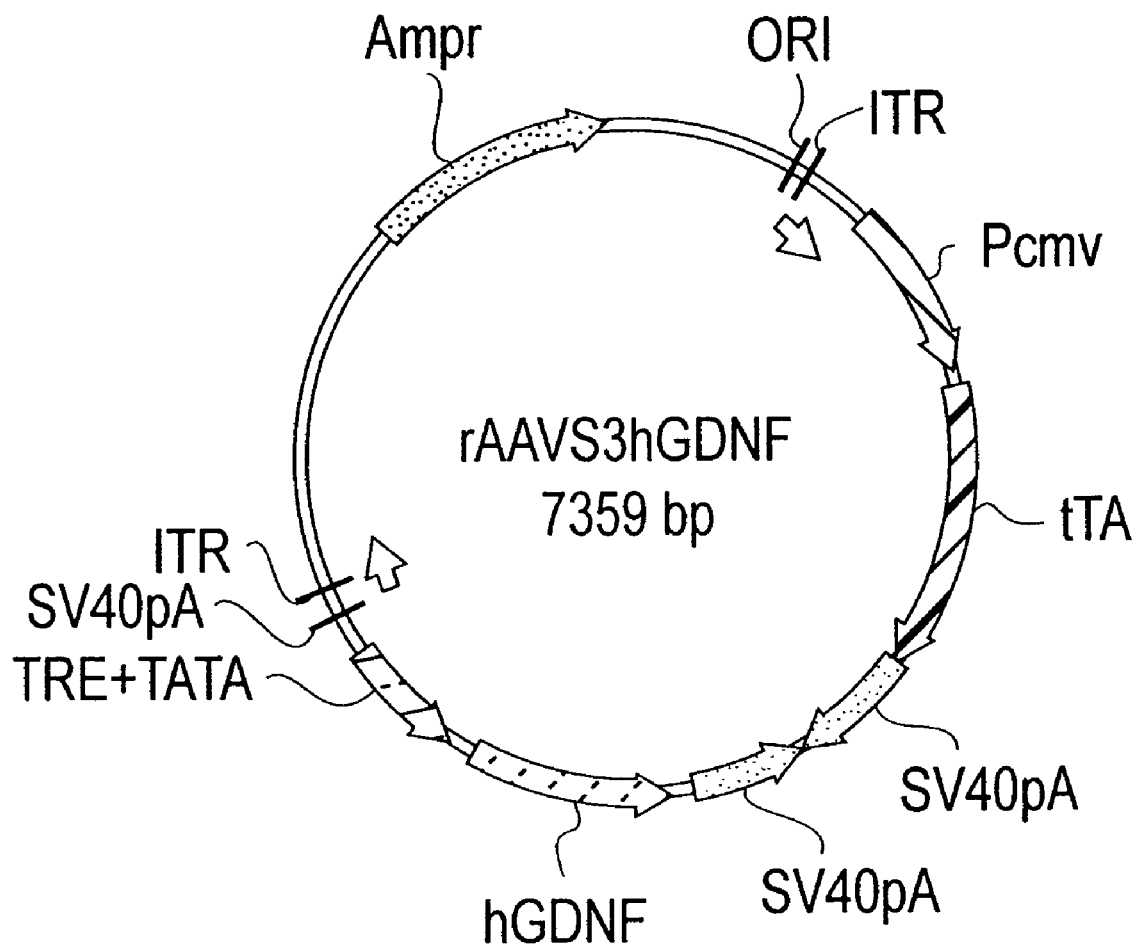
FIG. 1 is a map of a rAAV vector rAAVS3hGDNF of the present invention.

The present invention will utilize a rAAV vector for delivery of therapeutic genes to the nervous system. The rAAV vector includes a regulatable promoter system for temporally regulating gene expression.

The practice of the present invention will employ, unless otherwise indicated, conventional methods of virology, microbiology, molecular biology and recombinant DNA techniques within the skill of the art. Such techniques are explained fully in the literature. See, e.g., Sambrook, et al. Molecular Cloning: A Laboratory Manual (Current Edition); DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, vol. I & II (P. Tijssen, ed.); Fundamental Virology, 2nd Edition, vol. I & II (B. N. Fields and D. M. Knipe, eds.) All references cited herein are incorporated by reference.

Definitions

The term "nucleic acid" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides, conservatively modified variants thereof, complementary sequences, and degenerate codon substitutions that have similar binding properties as the reference nucleic acid and are metabolized in a manner similar to naturally occurring nucleotides.

The terms "nucleic acid," "nucleic acid molecule," "nucleic acid fragment," "nucleic acid sequence or segment," or "polynucleotide" are used interchangeably.

The term "gene" is used broadly to refer to any segment of nucleic acid associated with a biological function. Thus, genes include coding sequences and/or the regulatory sequences required for their expression. For example, "gene" refers to a nucleic acid fragment that expresses mRNA, functional RNA, or specific protein, including regulatory sequences. "Genes" also include non-expressed DNA segments that, for example, form recognition sequences for other proteins. "Genes" can be obtained from a variety of sources, including cloning from a source of interest or synthesizing from known or predicted sequence information, and may include sequences designed to have desired parameters.

The term "gene delivery" or "gene transfer" refers to methods or systems for reliably inserting foreign DNA into target cells, such as into cells of the central and peripheral nervous systems. Such methods can result in transient or long term expression of genes. Gene transfer provides a method for the treatment of acquired and inherited diseases.

The term "vector" refers to any genetic element, such as a plasmid, phage, transposon, cosmid, chromosome, virus, virion, etc., which is capable of replication when associated with the proper control elements, such as a helper virus, and which can transfer gene sequences between cells. Thus, the term includes cloning and expression vehicles, as well as replication-defective viral vectors.

The term "AAV vector" refers to a vector derived from an adeno-associated virus serotype, including without limitation, AAV-1, AAV-2, AAV-3, AAV-4, AAV-5, AAVX7, etc. "rAAV vector" refers to a vector that includes AAV nucleotide sequences as well as heterologous nucleotide sequences. rAAV vectors require only the 145 base terminal repeats in cis to generate virus. All other viral sequences are dispensable and may be supplied in trans (Muzyczka, (1992) *Curr Topics Microbiol. Immunol.* 158:97). Typically, the rAAV vector genome will only retain the inverted terminal repeat (ITR) sequences so as to maximize the size of the transgene that can be efficiently packaged by the vector. The ITRs need not be the wild-type nucleotide sequences, and may be altered, e.g., by the insertion, deletion or substitution of nucleotides, as long as the sequences provide for functional rescue, replication and packaging.

The term "recombinant AAV virion," or "rAAV virion" refers to an infectious, replication-defective virus composed of an AAV protein shell, encapsidating a DNA molecule of interest which is flanked on both sides by AAV ITRs. A rAAV virion is produced in a suitable producer cell which has had an AAV vector, AAV helper functions and accessory functions introduced therein. In this manner, the producer cell is rendered capable of encoding AAV polypeptides that are required for packaging the AAV vector (containing a recombinant nucleotide sequence of interest) into recombinant virion particles for subsequent gene delivery.

The term "transduction" refers to the delivery of a DNA molecule to a recipient cell either in vivo or in vitro, via a replication-defective viral vector, such as via a recombinant AAV virion.

The term "transfection" is used to refer to the uptake of foreign DNA by a mammalian cell. A cell has been "transfected" when exogenous DNA has been introduced inside the cell membrane. Transfection can be used to introduce one or more exogenous DNA moieties, such as a plasmid vector and other nucleic acid molecules, into suitable cells. The term refers to both stable and transient uptake of the genetic material.

The terms "tetracycline-off" and "tet-off" refer to a tetracycline inducible promoter system including tetracycline response elements that allow transcription of a nucleic acid that is operatively linked to the promoter system in the absence of doxycycline or tetracycline, and related compounds. In the presence of doxycycline or tetracycline transcription of the operatively linked nucleic acid is turned "off" in a non-leaky promoter system. The term "non-leaky" refers to control of expression of the operatively linked nucleic acid so that in the presence of doxycycline or tetracycline, expression of the nucleic acid is about 10%, preferably about 5%, or less in comparison to expression of the nucleic acid in the absence of doxycycline or tetracycline.

The term "tetracycline-controlled transactivator" (tTA) refers to a fusion protein used to control nucleic acid expression in the presence or absence of doxyclycline, tetracycline and related compounds. The tTA includes a tet repressor (tetR) fused to any domain capable of activating transcription. The tTA may include a tetR fused to a C-terminal portion of VP16, including tTA1, tTA2, tTA3, tTA4, etc. (See Baron, U. et al., *Nuc. Acid Res.,* 25(14): 2723-2729, 1997.)

The term "Kozak-like sequence" refers to a sequence for facilitating the initial binding of mRNA to the small subunit of the ribosome for initiation of translation. An exemplary sequence is GCCRCCATGG where R is a purine (A or G) (SEQ ID NO: 25). One, two, three or more nucleotides may be substituted in the exemplary Kozak-like sequence. (Kozak, M., *Cell,* 44(2):283-92, 1986; Kozak, M. *Nucleic Acids Res., October* 26; 15(20):8125-48, 1987; Kozak, M, *J. Biol. Chem.,* 266(30): 19867-19870, 1991.) One, two, three or more nucleotides may be substituted in the Kozak-like sequence.

The term "therapeutically effective amount" refers to an amount of nucleic acid product that is nontoxic but sufficient to provide the desired effect and performance at a reasonable benefit/risk ratio attending any medical treatment.

The term "treating" refers to ameliorating at least one symptom of a disease or a condition.

The term "nervous system" refers to the "central nervous system" and the "peripheral nervous system." As used herein, "central nervous system" should be construed to include brain and/or the spinal cord of a mammal, including motor neurons. The term may also include the eye and optic nerve in some instances. The term includes, but is not limited to, neuronal cells, glial cells, astrocytes, cereobrospinal fluid (CSF), interstitial spaces, bone, cartilage and the like. "Peripheral nervous system" includes sensory neurons, sympathetic neurons and parasympathetic neurons.

The terms "nervous system disorder" and "nervous system disease" refer to both hereditary and sporadic conditions that are characterized by nervous system dysfunction, and which may be associated with atrophy of the affected central or peripheral nervous system structures, or loss of function without atrophy. Neurodegenerative diseases and disorders include but are not limited to amyotrophic lateral sclerosis (ALS), hereditary spastic hemiplegia, primary lateral sclerosis, spinal muscular atrophy, Kennedy's disease, Alzheimer's disease, Parkinson's disease, multiple sclerosis, dysfunction in ganglioside storage or demyelination, such as Tay-Sachs disease, G1 gangliosidosis, metachromatic leukodystrophy, Sandhoff's disease, Hurler's syndrome and related mucopolysaccharidoses and Krabbe's disease, and repeat expansion neurodegenerative diseases, e.g., diseases associated with expansions of trinucleotide repeats such as polyglutamine (polyQ) repeat diseases, e.g., Huntington's disease (HD), spinocerebellar ataxia (SCA1, SCA2, SCA3, SCA6, SCA7), spinal and bulbar muscular atrophy (SBMA), and dentatorubropallidoluysian atrophy (DRPLA). Disorders affecting the nervous system may also include spinal cord injury, stroke, trauma, and tumors.

Regulatable rAAV Vector

The vector of the present invention is a recombinant adeno-associated viral vector which includes the ITRs of AAV. The vector also includes a tet regulatable promoter system, and a therapeutic nucleic acid.

In a preferred embodiment of the present invention, ITRs from AAV2 are provided in a vector and the ITRs flank the tet-regulatable promoter system and the therapeutic nucleic acid. Preferably all other AAV sequences are deleted from the rAAV vector. The ITRs may be wild-type or recombinant and the ITRs do not need to be identical as long as the ITRs allow for packaging of the virions.

The tet system may be used to regulate expression of the therapeutic nucleic acid. As discussed above, the preferred tet-regulatable system of the present invention minimizes the leaky regulation of the therapeutic nucleic acid.

Figure 2:
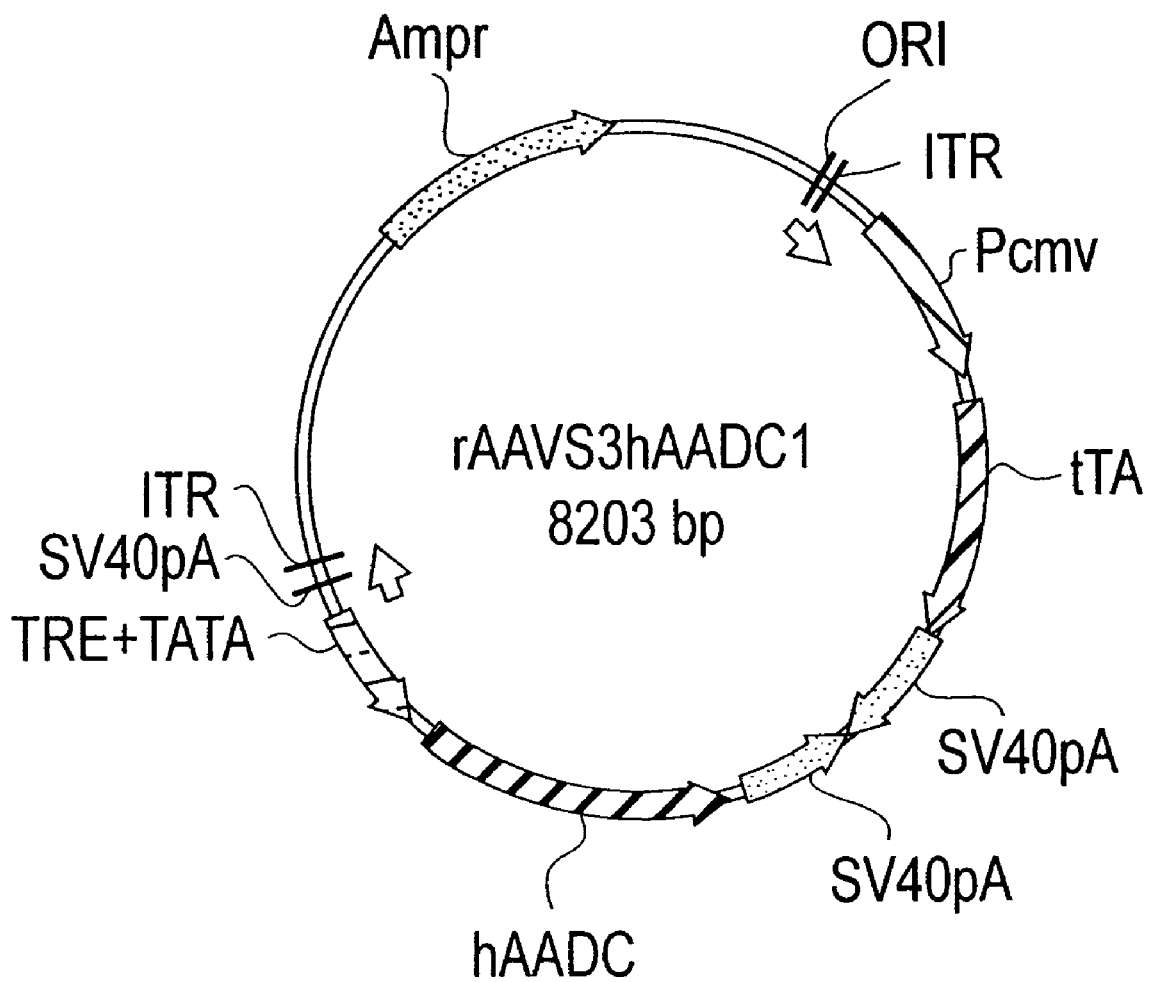
FIG. 2 is a map of a rAAV vector rAAVS3hAADC of the present invention.
Figure 3:
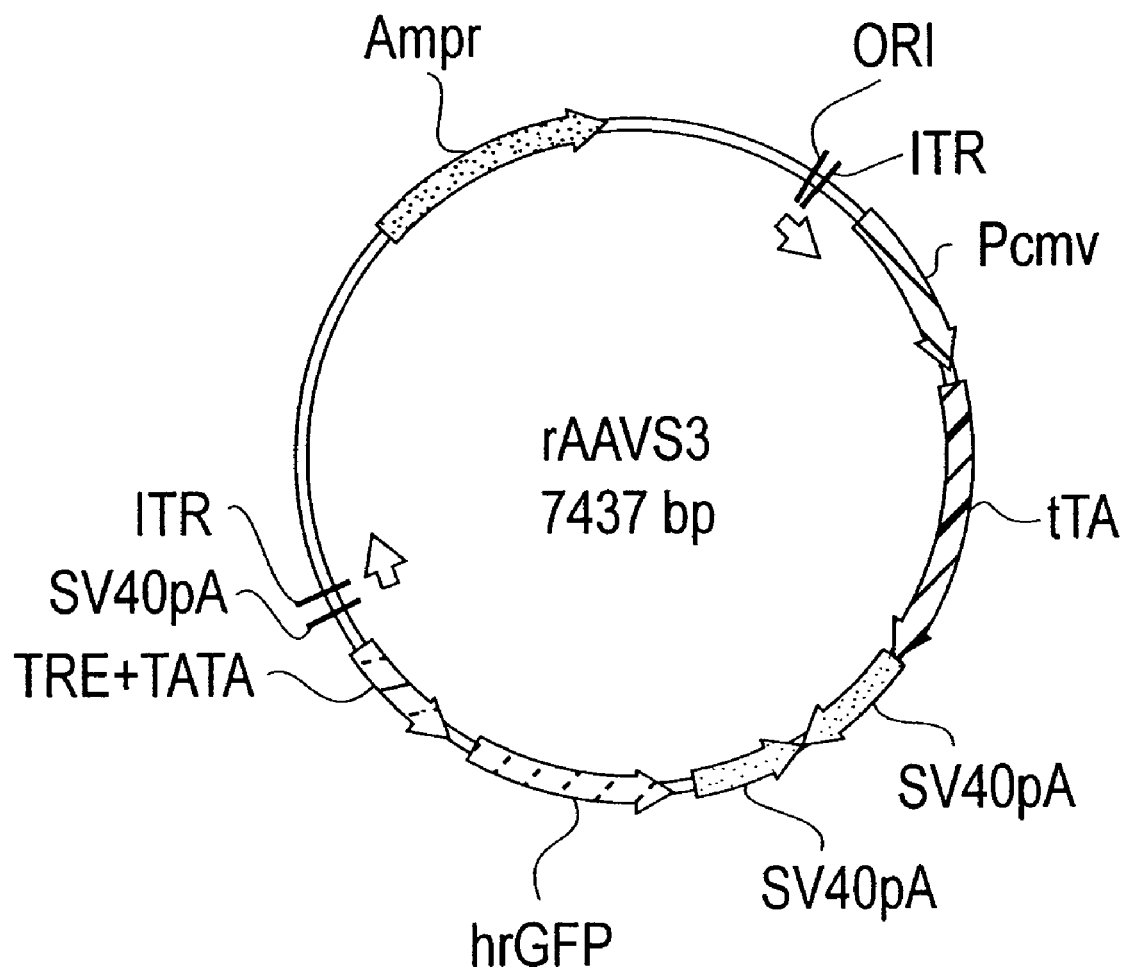
FIG. 3 is a map of a rAAV vector rAAVS3 of the present invention
Figure 4:
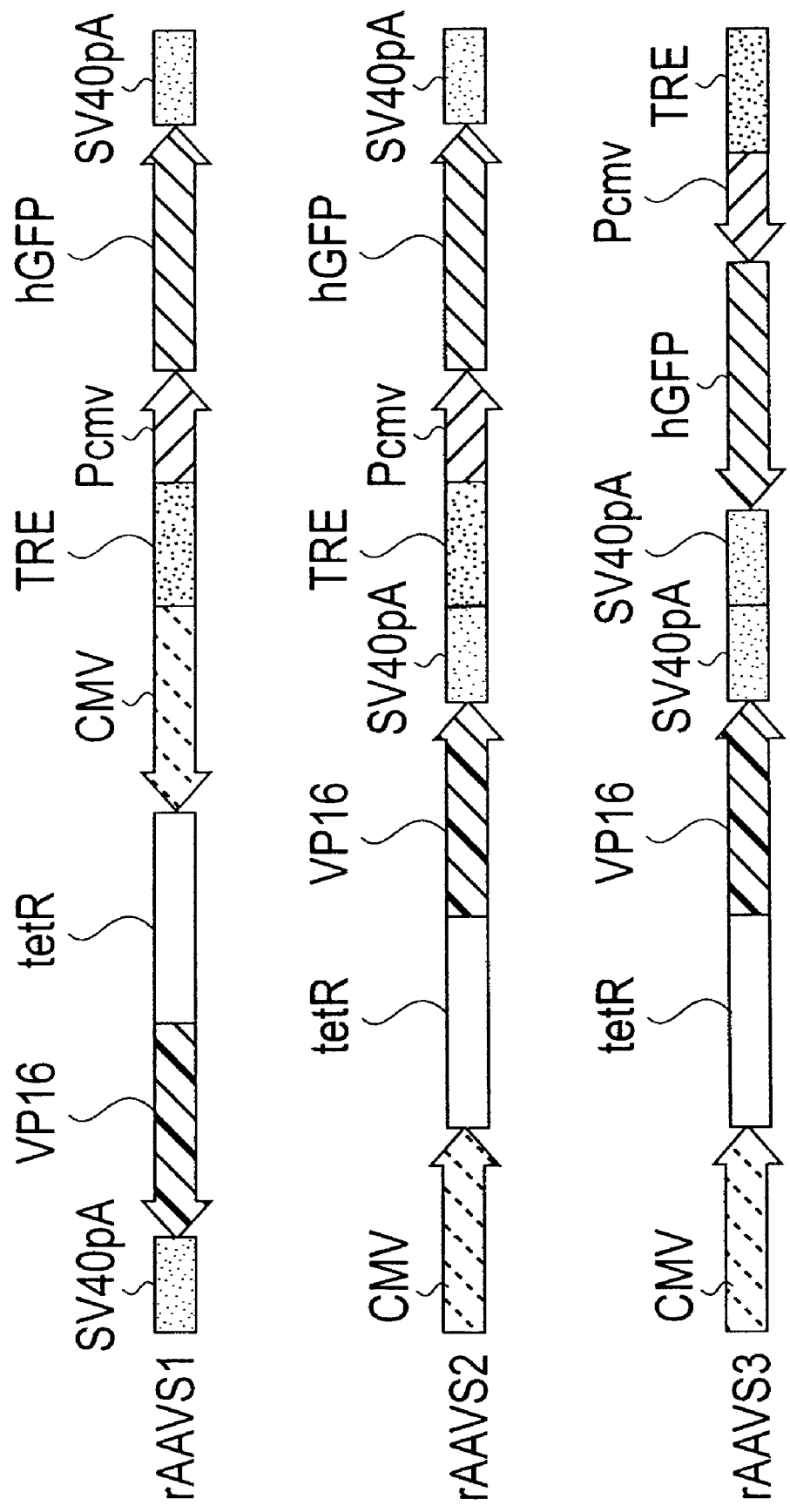
FIG. 4 is a schematic representation of three rAAV vectors illustrating orientation of the expression cassettes.
Figure 5A:
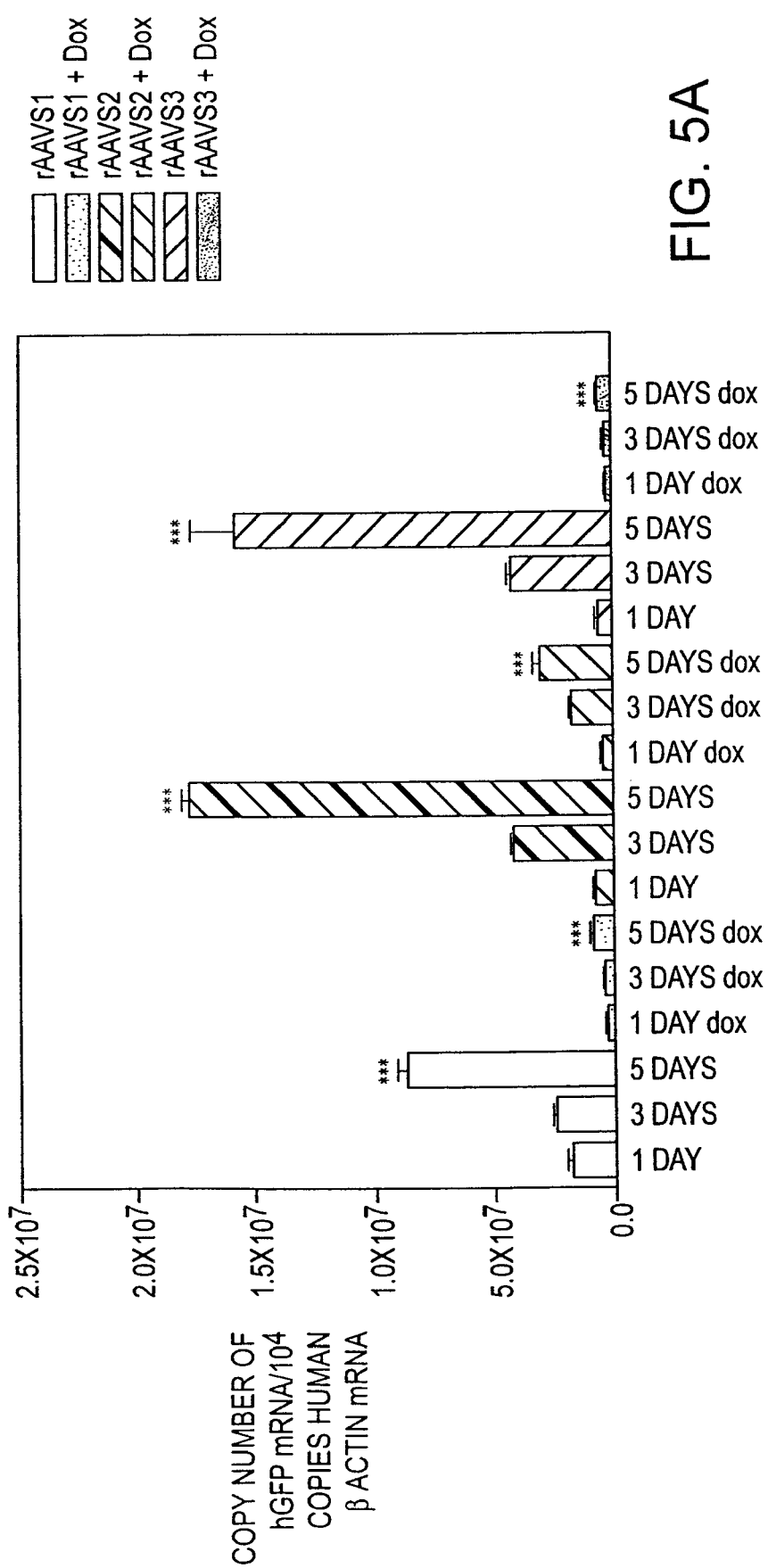
FIG. 5A shows the copy number of hGFP mRNA normalized to β-actin RNA for three rAAV vectors in the presence or absence of dox.
Figure 5B:
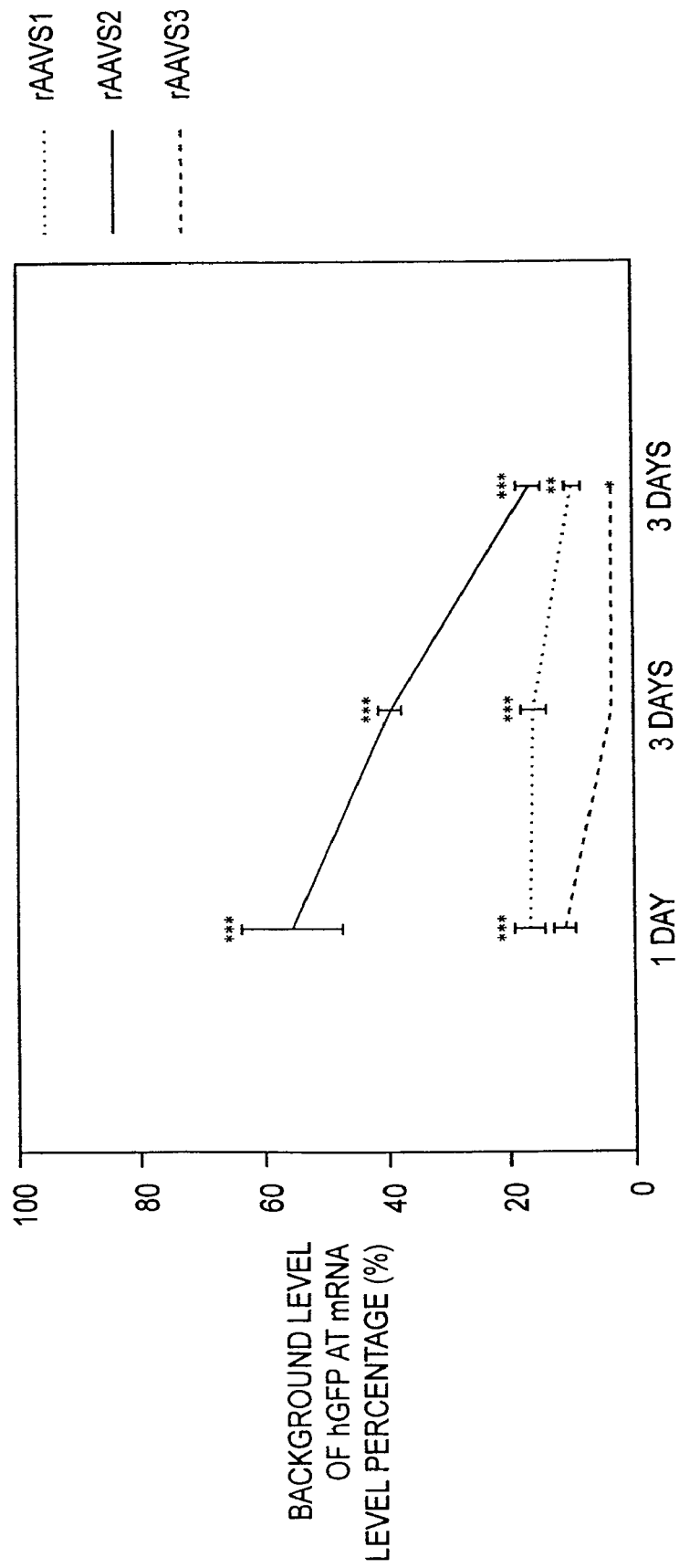
FIG. 5B shows the level of inhibition by dox at the mRNA level for three rAAV vectors.

To exemplify the invention, a rAAV vector, rAAVS3, is constructed as follows. One of skill in the art will understand that alternative promoters, enhancers, other regulatory elements, and therapeutic nucleic acids may be used in the construction of the tet-regulatable rAAV vector of the present invention. As shown in FIGS. 1-3, the preferred rAAVS3 vector includes a cytomegalovirus (CMV) promoter, a tetracycline-controlled activator (tTA), a minimal CMV promoter ($P_{CMV}$), a tet response element (TRE), a Simian virus 40 polyadenylation signal (SV40pA), and a therapeutic nucleic acid, flanked by AAV ITRs from AAV2. In order to control regulation of the therapeutic nucleic acid, the expression cassettes for the therapeutic nucleic acid and the tTA are driven in opposite directions, away from the ITRs and towards each other. The expression cassette for the therapeutic nucleic acid includes the TRE having seven copies of the tet resistance operator binding sites in frame with the $P_{CMV}$ driving the therapeutic nucleic acid, followed by the SV40pA. The tTA expression cassette includes the CMV promoter driving a tet repressor (tet R) in frame with a nucleic acid encoding the C-terminal 127 amino acids of the herpes simplex virus VP16 activation domain (VP16) and terminating in SV40pA. Tight regulation provided by the rAAVS3 vector is shown in FIGS. 5A and 5B in comparison to two vectors, rAAVS1 and rAAVS2, having the same expression cassettes, but driven in alternative directions to rAAVS3 (constructs shown in FIG. 4). In rAAVS1, the therapeutic nucleic acid and the tTA expression cassettes are driven away from each other and toward the ITRs. In rAAVS2, the therapeutic nucleic acid and tTA expression cassettes are driven in the same direction. As will be described in the examples below, in comparison to rAAVS1 and rAAVS2 vectors, the rAAVS3 vector can be used to tightly regulate expression of the therapeutic nucleic acid, providing a non-leaky promoter system with about 10% or less, preferably with about 5% or less expression in the "OFF" state compared to the "ON" state, more preferably with about 1% or less expression in the "OFF" state compared to the "ON" state.

In some embodiments, the rAAV vector may include a Kozak-like consensus sequence to facilitate expression of the therapeutic nucleic acid. (See, for example, Kozak, M, *J. Biol. Chem.*, 266(30): 19867-19870, 1991.) Exemplary Kozak-like consensus sequences are described in the examples below. Any Kozak-like consensus sequence may be included in the rAAV vectors of the present invention and the sequences are not limited to the examples given below.

In a preferred embodiment, the therapeutic nucleic acid encodes a product for treatment of a nervous system disorder. The product may be, by way of example, but not limited to, a protein or an RNA molecule such as an inhibitory RNA molecules including ribozymes, antisense RNAs, small inhibitory RNAs (RNAi) and microRNAs.

Suitable nucleic acids include, but are not limited to, those encoding proteins for the treatment of nervous system disorders as described above. Suitable genes for the treatment of nervous system disorders, for example, using the rAAV vector of the present invention encoding, but not limited to, glial cell-line derived neurotrophic factor (GDNF) (Genbank HUMGDNF02; Accession No. L19063), and other members of the GDNF family including neurturin, perspephin and artemin, aromatic amino-acid decarboxylase (AADC) (Genbank HUMDDC, Accession No. M76180); (brain-derived neurotrophic factor (BDNF), nerve growth factor (NGF) (EMBL HSNGF2; Accession No. X53655, and/or other members of the neurotrophin factor family including neurotrophin (NT)-3 (Genbank HUMBDNF; Accession No. M37762) and NT-4 (Genbank HUMPPNT4P; Accession No. M86528), bone morphogenetic proteins such as BMP4, ciliary neurotrophic factor (CNTF), platelet-derived neurotrophic factor (PDGF), leukemia inhibitory factor (LIF), interleukins, such as IL-2 and IL-12, tyrosine hydroxylase (TH) (Genbank HUMTHX, Accession No. M17589), dopamine-β-hydroxylase (DBH), phenylethanolamine N-methyltransferase (PNMT), tryptophan hydroxylase, vesicular monoamine transporter (VMAT), dopamine transporter (DAT) and other neuronal transporters such as catecholamine, serotonin and glutamate transporters, vascular endothelial growth factor (VGEF).

Other suitable nucleic acids include superoxide dismutase (SOD1 or SOD2) (GenBank HUMCUZNDI; Accession No. M12367; for SOD-1, EMBL HSSOD2G, Accession No. X65965 for SOD-2), catalase (EMBL HSCATR, Accession No. X04076), and/or glutathione peroxidase (MBL HSG-SHPX, Accession No. Y00433); adenosine A-1 receptor (GenBank S56143; Accession S56143); glutamate decarboxylase (GenBank S61898; Accession S61898), choline acetyltransferase (ChAT), cholinergic nicotinic or muscarinic receptors, neuropeptides, including but not limited to enkephalin, dynorphin, substance P, neuropeptide Y, GABA-A receptor isoforms (EMBL HSGABAAA1; Accession X14766), calcium-dependent potassium channels (GenBank DROKCHAN, Accession M96840) and/or ATP-sensitive potassium channels (Ho, et al 1993 Nature 362:31-8).

Also included are nucleic acids involved in regulation of cell death such as bcl2 and other members of the bcl2 family such as, $bcl_{xl}$ and bax, and caspase enzymes and dominant-negative nucleic acids against caspase enzymes, and tumor necrosis related apoptosis-inducing factor (TRAIL). Nucleic acids encoding for molecules that stimulate or inhibit growth of neuronal processes, such as nogo, netrins, semaphorins, N-CAM, eph receptors and eph ligands, and artificial peptides that interfere with intracellular signaling mechanisms and transcription factors involved in neuronal growth and function such as sonic hedgehog (SHH), nurr-1, HOX genes, LIM genes, POU genes, c-fos and other members of the SP1 family, such as fosB are suitable for use in the present invention. The nucleic acids for use in the present invention include the deposited nucleic acids listed above as well as any nucleic acids having conservative substitutions, sufficient homology, or encoding RNA or the proteins listed above for the treatment of nervous system disorders.

The gene can code for a transmitter, such as acetylcholine or GABA, or a receptor for such a transmitter or a gene that encodes a growth factor such as FGF (fibroblast growth factor), EGF (epidermal growth factor), glial growth factor, PDGF (platelet-derived growth factor) or a cytokine, or the like.

Virion Production rAAV virions, which include the rAAVS3 vector, can be produced using standard methodology, known to one of skill in the art. The methods generally involve the steps of introducing the rAAV vector containing the therapeutic nucleic acid and an AAV-derived helper plasmid into a producer cell, where the helper construct includes AAV coding regions capable of being expressed in the producer cell to complement AAV helper functions missing from the rAAV vector wherein AAV helper functions include, but are not limited to, one, or both of the major AAV ORFs, namely the rep and cap coding regions, or functional homologues thereof; and helper functions from herpes virus or adenovirus, such as EA2, E3 and E4; and culturing the producer cell to produce rAAV virions. The AAV expression vector, AAV helper construct(s) can be introduced into the producer cell, either simultaneously or serially, using standard transfection techniques known to one of skill in the art (Zoltukhin et al., Gene Therapy, 6:973-985, 1999).

The virions are then harvested from the supernatant of transfected cells, isolated by freeze/thaw cycles and centrifugation. The virions may be purified by binding to a heparin-agarose column, eluted, and concentrated. For in vivo delivery, rAAV virions may be purified by fast performance liquid chromatography (FPLC).

Delivery of Virions to Target Cells

The rAAV virions formed from the tet-regulatable rAAV vectors may be delivered to target cells of the central or peripheral nervous system, or both, or any target cell from which the therapeutic protein can have an effect on a nervous system disorder. Preferably, the rAAV virions are added to the cells at the appropriate multiplicity of infection according to standard transduction methods appropriate for the particular target cells. Titers of rAAV virions to administer can vary, depending upon the target cell type and the particular viral vector, and may be determined by those of skill in the art without undue experimentation. rAAV virions are preferably administered to the cell in a therapeutically-effective amount. rAAV virions may be administered in a physiologically acceptable carrier. In general, a "physiologically acceptable carrier" is one that is not toxic or unduly detrimental to cells. Exemplary physiologically acceptable carriers include sterile, pyrogen-free, phosphate buffered saline. Physiologically-acceptable carriers include pharmaceutically-acceptable carriers.

The rAAV virions may be delivered to a target cell by any method known to one of skill in the art, including, but not limited to injection into the delivery site tissue. By way of example, for delivery to a specific region of the central nervous system, the rAAV virions may be administered by microinjection, infusion, convection enhanced delivery (CED), electroporation or other means suitable to directly deliver the composition directly into the delivery site tissue through a surgical incision. The delivery is accomplished slowly, such as at a rate of about 0.2-1 µl per minute. Pursuant to the invention, administration of rAAV virions into selected regions of a subject's brain may be made by drilling a hole and piercing the dura to permit the needle of a microsyringe or micropipette to be inserted. A stereotaxic apparatus may be used to assist in delivering the virions to the specific target cells. Alternatively, rAAV virions may be delivered by lumbar puncture, for example, to the cerebral spinal fluid or delivered intraventricularly. The rAAV virions can be injected intrathecally into a spinal cord region. In another example, virions may be delivered to muscle in order to deliver rAAV to the terminals of motor neurons or sensory neurons.

EXAMPLES rAAV Vector Construction

To determine the tet-off promoter system that provides non-leaky regulation of expression, three constructs were made. The three constructs differ in the orientation of the promoters used to drive expression of the operatively linked nucleic acid for each promoter. As will be described, the rAAVS3 provides a non-leaky tet-off promoter system in comparison to rAAVS1 and rAAVS2 which provide leaky tet-off promoter systems.

The pBR322-based shuttle vector pTR (Mark Sands, Washington University School of Medicine) was used for all three constructs rAAVS1, rAAVS2, and rAAVS3. pTR was digested with PstI and blunted by the large fragment of T4DNA polymerase. A 1.6 kb fragment isolated and ligated into the KpnI and NotI digested and blunted sites of pBluescript KS+ to make the pBSTR. This is a high copy number shuttle plasmid which contains two inverted terminal repeats (ITR) of AAV2 and an intervening stuffer region between the two ITRs.

To make each of the self-regulated shuttle plasmids, some intermediate plasmids were made in pSP72 (Promega Corporation. Madison, Wis., USA) and then appropriate expression cassettes were transferred into the pBSTR to replace the stuffer region. First, the EcoRI and SspI (blunted) IREShGFP fragment from pIRES-hGFP-1a (Stratagene, La Jolla, Calif., USA) was inserted into the EcoRI and EcoRV sites of pSP72 to make pSP721REShGFP. The TRE fragment was cut out of pTRE-2 (Clontech, Palo Alto, Calif., USA) with XhoI blunt-ended, and then cut with EcoRI. This fragment was ligated into the SmaI and EcoRI sites of pSP721R-EShrGFP to make pSP72TREIREShrGFP EcoRI and BstXI were used to remove the IRES fragment from this plasmid to produce pSP72TREhrGFP which is used for all of the constructs, rAAVS1, rAAVS2, and rAAVS3. For generation of the rAAVS1 construct, the blunted XhoI and PvuII tTA expression unit from plasmid pTet-Off (Clontech, Palo Alto, Calif., USA) was ligated into the blunted BamHI site of the pSP72TREhrGFP to make the pSP72ALL-. Following digestion of pSP72ALL—with BglII and XhoI, the ALL-double cassette was transferred into the blunted BglII sites of the pBSTR to make pTR-S1. To make the two other configurations of self-regulating shuttle plasmids pTR-S2 and pTR-S3 to be used for rAAVS2 and rAAVS3, another intermediate plasmid pBSTRTet-Off was made first. The blunted XhoI and PvuII tTA expression unit from pTet-Off was inserted into the SmaI and EcoRV sites of the pSP72 to derive plasmid pSP72tTA. BamHI and BglII were then used to cut the CMVtTA fragment from pSP72tTA and insert it into the BglII sites of pBSTR to produce pBSTRTetOff. The BglII and Xho TREhrGFP from pSP72TREhrGFP blunted into the HindIII site of pBSTRTet-Off to make TR-S2 and pTR-S3.

Construction of S3hAADC rAAV Vector

The human AADC cDNA was cut out of pBluescript by EcoRV and a partial digestion with Not I (plasmid a gift of Dr. Krys Bankiewicz, UCSF). One skilled in the art will recognize that hAADC cDNA may be obtained from any source for use with the present invention. The 1.5 kb hAADC fragment was inserted into EcoRV and Not I digested S3hGFP plasmid (described above) to make S3hAADC. The orientation of the expression cassettes is as described above for the rAAVS3 vector. The S3hAADC plasmid was used to produce S3hAADC rAAV2 virus.

Construction of S3hGDNF rAAV Vector

A hGDNF cDNA was amplified from human fetal astrocytes in the laboratory of Dr. Martha C. Bohn and will be cloned into the S3-hGFP shuttle plasmid to replace hGFP using techniques commonly known to one of skill in the art. (See, e.g., Sambrook, et al. Molecular Cloning: A Laboratory Manual (Current Edition).) The orientation of the expression cassettes will be as described above for the rAAVS3 vector. The S3hGDNF plasmid will be used to produce S3hGDNF rAAV2 virus.

Construction of rAAV Vectors Including a Kozak-Like Consensus Sequence

In some embodiments, rAAV vectors were constructed to include a Kozak-like sequence to facilitate initiation of transcription of the gene of interest. PCR primers were used to amplify GDNF from human RNA. Three S3hGDNF plasmids were constructed having different Kozak-like consensus sequences (S3hGDNFkzk 2, 3 and 4, primers shown in Table 2, below). An additional plasmid, S3hGDNF without a Kozak-like consensus sequence similar to the S3hGDNF plasmid described above was constructed using the PCR primers shown in Table 2 (S3hGDNFkzk1). Each of the plasmids was amplified using unique sets of forward and reverse primers for the Kozak-like consensus sequence, and common forward and reverse primers of the GDNF gene (GDNF internal primer pair). Orientation of the S3hGDNFkzk constructs is similar to the S3 rAAV construct shown in FIG. 1 and described above with the ITRs flanking the coding sequences. An S3rGFPkzk plasmid was also constructed using the primers shown below. Standard PCR protocols were used to amplify the DNA fragments with or without Kozak-like consensus sequences as will be understood by one skilled in the art. The PCR products were cloned into a commercially available shuttle vector, followed by subcloning into the S3hAADCrAAV vector described above from which the AADC gene has been removed. Standard cloning techniques were used to clone the S3hGDNFkzk 1-4 plasmids.

Recombinant AAV Virion Production

The components needed for the production of recombinant AAV-2 particles in the helper virus-free system include a shuttle plasmid containing the gene of interest and AAV-2 ITRs, a packaging plasmid known to one of skill in the art for clinical applications, and 293T cells. Recombinant AAV (rAAV) vectors were packaged and purified as described previously with minor modifications (Zoltukhin et al., Gene Therapy, 6:973-985, 1999). In brief, 293T cells were plated at $2\times10^6$ cells per 100-mm tissue culture plate in 10 ml DMEM containing 10% FBS and antibiotics 48 h prior to transfection. Shuttle and pDG, plasmids were used at a ratio of 1:3 for $CaCl_2$ transfection. (pDG is a type of packaging plasmid known as "the pDG plasmid 29", generously provided by Juergen Kleinschmidt, University of Heidelberg, which has been used in the laboratory, however, any packaging plasmid may be used.) At 2-4 h before transfection, fresh, prewarmed medium was added to the 293T cells and then the DNA/$CaCl_2$/HPES suspension was added dropwise, swirling gently to distribute the DNA suspension evenly. After 48 h, the medium was replaced with 10 ml of fresh DMEM growth medium and plates were incubated for another 24 h. After 72 h incubation, the cells were harvested into 50-ml falcon tubes and 15 ml lysis buffer (50 mM Tris-HCl (pH 8.5) and 150 mM sodium chloride) was added to 20 plates worth of cells.

The cell suspension was subjected to three rounds of freeze/thawing by alternating tubes between a dry ice-ethanol bath and a 37° C. water bath, vortexing briefly after each thaw. Following centrifugation at 10 000 g for 10 min at room temperature, the supernatant was transferred to a fresh tube and 4 µl of benzonase (50 U/µl) was added to the cell suspension. After incubation at 37° C. for 30 min, the lysate was clarified by centrifugation at 5000 g for 10 min and the crude viral lysate loaded onto a 15-60% iodoxanol step gradient and centrifuged at 69 000 g for 1 h and 20 min at 18° C. After centrifugation, 4 ml of the 40% fraction was collected by puncturing the sidewall of the ultracentrifuge tube with an 18 G needle. This fraction was loaded onto heparin-agarose column, which was preequilibrated with 20 ml PBS-MK buffer (1× phosphate-buffered saline (PBS), 1 mM $MgCl_2$ and 2.5 mM KCl). The rAAV particles were eluted with 4.0 ml PBS containing 1 M NaCl and concentrated using an Ultrafree-4 Bio-Max-100 membrane. After concentrating the sample to 0.5 ml and dialyzing the sample overnight against PBS, the rAAV vector capsid particle number was determined using an ELISA kit (Progen Biotechnik GMBH, Heidelberg, Germany) based on the A20 capsid protein and checked for in vitro expression of GFP using 293T cells. The final particle titer of rAAVS1 was $4.0\times10^{12}$ viral particles per milliliter, $1.3\times10^{12}$ viral particles per milliliter for rAAVS2, $1.8\times10^{12}$ viral particles per milliliter for rAAVS3.

For the in vivo studies, rAAVS3 vectors of the preferred embodiment were purified by FPLC. In brief, the lysate of harvested cells was applied to a POROS-PI ion-exchange column (Waters, Inc.) and then eluted with 350 mM potassium chloride (Kaludov et al., Hum. Gene Ther., 13: 1235-1243, 2002). The eluant was then applied to a HiTrap heparin column (Amersham, N.J., USA) and eluted with a zero to 1 M sodium chloride gradient (Clark et al., Hum. Gene Ther., 10: 1031-1039, 1999). The buffer was exchanged to PBS and vector stocks concentrated using a CentriPlus 100 000 MW cut-off filter. The titer of the final stock was measured by Q-PCR as described elsewhere (Veldwijk et al., *Mol. Ther.*, 6: 272-278, 2002).

Viral Infection and hGFP Regulation by Dox Under in Vitro Conditions

To evaluate the regulation of hGFP transgene expression of the different vectors, the recombinant AAV2 viruses (rAAVS1, rAAVS2 and rAAVS3) were used to infect wtAd5 superinfected 293T cells at MOI 100. At 4 h after viral infection, 2 µg/ml of dox was added to half the wells (n=3) to suppress the hGFP expression, and the remaining cells were allowed to grow in normal medium to allow maximal expression of hGFP.

After 3 days of growth in the absence of dox, robust expression of hGFP and a high percentage of hGFP-positive cells were observed by florescence microscopy. In contrast, only a very few, weakly positive cells were observed in cells grown in the presence of dox. The expression level of hGFP was quantitatively assessed by FACS analysis using a Becton Dickinson (San Jose, Calif., USA) FACScan. Consistent with the microscopic observations, all three viruses showed a high level of hGFP expression in the "ON" phase. However in the "OFF" phase, only a very low level of hGFP fluorescence was observed in cells infected with non-leaky rAAVS3, whereas the number of positive cells and the total fluorescence from cells infected with rAAVS1 or rAAVS2 was much higher.

Time Course Evaluation of Transgene Expression at the Protein Level by Flow Cytometry Using FACS analysis, a time course at 1, 3 and 5 days after infection of transgene expression in the presence or absence of dox was conducted. The cells were applied to the Beckman Coulter Elite ESP flow cytometer for cell sorting 48 h after the viral infection. The hrGFP-positive cells were collected and expanded in normal DMEM medium. For a time course of transgene turn-off, cells were seeded into six wells plates at varying densities so that cells would attain approximately the same density at each time point after growth for 1, 3, 5 or 7 days in medium containing 2 µg/ml of Dox. Cells were then collected, fixed in 4% PFA and resuspended in PBS buffer for FACScan analysis.

The highest expression of hGFP from all vectors was at 3 days post-transduction (P<0.001). Cells infected with the preferred tet-off promoter system, rAAVS3, showed the lowest level of background expression in the presence of dox, 0.65% at 1 day, 2.13% at 3 days and 0.54% at 5 days postinfection. In contrast, rAAVS2 conferred high background expression, 15.90% at 1 day, 29.95% at 3 days and 36.67% at 5 days (P<0.001, rAAVS2 versus rAAVS3 at all three time points). The ability to regulate transgene expression from rAAVS1 was in between rAAVS3 and rAAVS2 (P<0.001, rAAVS1 versus rAAVS3 at 3 and 5 days.

A dose-response curve of dox regulation from rAAVS3 was also generated. This showed that this self-regulated vector display dose-dependent regulation as has been reported for the tet-off system at the plasmid level (Baron et al., *Methods Enzymol.*, 327: 401-421, 2000).

In addition to testing these vectors in 293T cells at MOI 100, the rAAVS3 vector was also tested at 10 and 300 MOI on 293T cells with similar results and at 100 MOI on Hela and HT1080 cell lines. Levels of expression were lower in these cell lines due to the absence of helper virus, but S3 also conferred the tightest regulation similar to that observed in 293T cells as assessed by flow cytometry.

Based on the sorted rAAVS3-infected stable cell line, transgene expression was consistently on before addition of inducer. However, up to 99% of the transgene expression could be turned off by 7 days when these cells were exposed to the inducer (2 µg/ml of Dox) continuously.

In Vitro Regulation of the Transgene at the mRNA Level

For QRT PCR, total RNA from cells infected in vitro with the different viruses at different time points and microdissected injected striatum were extracted using Tri Reagent (Sigma, T9424). Total RNA was treated with Rnase-free DNase I (Boehringer Mannheim) at a concentration of 1 U/µg of total RNA at room temperature for 30 min to remove the contaminating DNA followed by heat inactivation at 75° C. for 15 min. The possible contamination by ssDNA from the rAAV vector DNA was removed by the incubation with restriction enzyme HaeIII (New England Biolabs, Inc., Beverly, Mass., USA) at 37° C. for 20 min. The resulting RNA was further purified using RNA Easy Kit (Qiagen Inc. CA, USA), according to the manufacturer's instructions.

Quantitative analysis of the expression of hGFP mRNA from samples was assessed using the Perkin Elmer 7700 System (Perkin-Elmer/Applied Biosystems, Inc., Foster City, Calif., USA). Using this method, quantitation is achieved by the addition of a fluorescently labeled probe which anneals between the forward and reverse primers of the target gene. The probe consists of an oligonucleotide with a fluorescent reporter dye (6-carboxylfluorescein, FAM) covalently linked to the 5' end and a quencher carboxytetramethylrhodamine (TAMRA) linked to the 3' end. During each PCR cycle, the 5' nucleotidase activity of the Taq enzyme will release the reporter dye from the probe. This results in the release and detection of fluorescent signal from the quencher dye. This fluorescent signal increases with each PCR cycle and quantitation is based on the threshold cycle, that is, the PCR cycle in which the amplification signal is first detected to be above the baseline signal (Kozlowski et al., *Mol. Ther.*, 3: 256-261, 2001.) In one QRT-PCR reaction, 25 ng template RNA was added to a 96-well plate which contained the following components from TaqMan Core PCR Kit (Perkin-Elmer/Applied Biosystems, Inc., Foster City, Calif., USA) 5 µl 10× TaqMan Buffer A (composed of 500 mM KCl, 100 mM Tris-HCl, 0.1 M EDTA, 600 nM passive reference dye, pH 8.3 at room temperature), 10 µl of 25 mM $MgCl_2$, 1.5 µl of each dNTP (10 mM for dATP, dCTP and dGTP, 20 mM for dUTP), 0.5 µl of forward and reverse primers (10 mM), 1 µl of 5 mM TaqMan probe, 0.25 µl (12.5 U) of RNAse Inhibitor and 0.25 µl (12 U) of MMuLV. RNAse-free water was added to bring the final volume of the reaction to 50 µl. The QRT-PCR amplification conditions were 30 min at 48° C., then 15 min at 95° C., followed by 40 cycles of denaturation at 95° C. for 15 s and annealing/extension at 59° C. for 60 s for all three genes evaluated in this study.

To determine the copy number of hGFP mRNA in the samples, the gene hGFP was inserted into the pBluescript KS downstream of the universal T7 promoter. SmaI digestion was used to linearize the plasmid and this DNA was used as template to carry out the hGFP in vitro transcription with the AmpliScribe T7 High Yield Transcription Kit (Epicenter Inc., Madison, Wis., USA). The copy number of hGFP mRNA per microgram was calculated according to the molecular weight of the hGFP sequence and Avogadro's number. Between 150 and 5 million copies of hGFP RNA were analyzed as the template in the 7700 PCR mix. This experiment was run in triplicate and the resulting threshold cycles for each known amount of hGFP were averaged and plotted to generate a regression equation. The resulting threshold cycles from in vitro samples were incorporated into this equation to obtain the number of copies of hGFP mRNA. In addition, levels of tTA mRNA and human β-actin mRNA were also analyzed and standard curves were developed in the same manner. Human β-actin was used as an internal control to normalize the results of hGFP and tTA mRNAs in each sample. Vector regulation at the mRNA level and the ratio of tTA under "ON" condition against the "OFF" condition were based on the normalized copy number of each sample. The sequences of the primers and probes for these three genes are SEQ ID NOS 1-9 listed in Table 1.

Quantitative analysis of the expression of GDNF mRNA and vector DNA will be achieved with the Real Time Quantitative RT-PCR & PCR 7700 System (Perkin-Elmer/Applied Biosystems, Inc.) as described above for hGFP. For both PCR and RT-PCR 25 ng of template (total RNA or DNA) will be added to a 96-well plate which contains the following reaction mix from the TaqMan PCR Kit (Perkin-Elmer/Applied Biosystems, Inc.): 5 ml of 10× TaqMan Buffer A (composed of 500 mM KCl, 100 mM Tris-HCl, 0.1 M EDTA, 600 nM passive reference dye, pH 8.3 at room temperature), 10 ml of 25 mM MgCl2, 1.5 ml of each dNTP (10-20 mM), 0.5 ml of forward and reverse primers (10 mM; see Table 1, SEQ ID NO: 13 and 14), 1 ml of the appropriate TaqMan probe (5 mM), and 0.25 ml (1.25 units) of AmpliTaq Gold. PCR water will be added to bring the total volume of the reaction to 50 ml. For RT-PCR, total RNA, will be treated with RNase-free DNase I (Boehringer Mannheim) for 30 min at room temperature followed by inactivation for 15 min at 75° C. RNA template (25 ng) will be reverse transcribed with 0.25 ml (12 units) of MMuLV. In addition, 1 ml of RNase inhibitor will be added to the reaction mix. RT-PCR cycle parameters were 48° C. for 30 min, 95° C. for 15 min, and 40 cycles of 95° C. for 15 s and 59° C. for 1 min.

For PCR, genomic DNA (25 ng) will be added to the PCR mixture and amplified using the following cycle parameters: 50° C. for 2 min, 95° C. for 10 min, and 40 cycles of 95° C. for 15 s and 59° C. for 1 min. To determine the number of copies of the hGDNF gene present in the sample a standard curve will be developed using the hGDNF gene isolated from a plasmid (pBSDSAhGDNF). The number of copies of hGDNF per microliter will be quantified using the molecular weight of the sequence and Avogadros' number. Between 100 and 10 million copies of hGDNF DNA will be analyzed as the template in the 7700 PCR mix. This will be run in triplicate and the resulting threshold cycles for each known amount of hGDNF will be averaged and plotted to generate a regression equation. The resulting threshold cycles from the injected caudate samples will then be put into this equation to obtain the number of copies of the hGDNF. This number will be then corrected for the total injection sample assayed. As an internal control, human β-actin will also be analyzed and a standard curve developed in the same manner using a TaqMan DNA Template Reagents Kit (Applied Biosystems). The resulting data will be expressed as the number of copies of the hGDNF gene in the entire injection site sampled per 10,000 copies of the β-actin gene.

mRNA for hAADC is detected using real time RT-PCR using the same method as described above for hGFP. The forward and reverse primers for AADC are shown in Table 1, SEQ ID NO: 10 and 11, respectively.

TABLE 1

| hrGFP | | | |
|---|---|---|---|
| Forward Primer | ACCTGATCGAGGAGATGTTCGT | SEQ ID NO: | 1 |
| Reverse Primer | AGGCCGGTGATGGTCTTCTT | SEQ ID NO: | 2 |
| Probe | CAAGGGCCGCAACTTCCCCAAC | SEQ ID NO: | 3 |
| tTA | | | |
| Forward Primer | TCGACGCCTTAGCCATTGA | SEQ ID NO: | 4 |
| Reverse Primer | TCGCGATGACTTAGTAAAGCACAT | SEQ ID NO: | 5 |
| Probe | AGAATAGGCACCATACTCACTTTTGCCCTTTAGAAG | SEQ ID NO: | 6 |
| B-Actin | | | |
| Forward Primer | TCACCCACACTGTGCCCATCTACGA | SEQ ID NO: | 7 |
| Reverse Primer | CAGCGGAACCGCTCATTGCCAATGG | SEQ ID NO: | 8 |
| Probe | ATGCCCTCCCCCATGCCATCCTGCGT | SEQ ID NO: | 9 |
| hAADC | | | |
| Forward Primer | GCAGGCAGTGCATTCATCTG | SEQ ID NO: | 10 |
| Reverse Primer | CAGTCAAAATTCACCAATAGCCAT | SEQ ID NO: | 11 |
| Probe | CTGAGTTCCGGCACCTTCTGAATGGA | SEQ ID NO: | 12 |
| hGDNF | | | |
| Forward Primer | CTGACTTGGGTCTGGGCTATG | SEQ ID NO: | 13 |
| Reverse Primer | TTGTCACTCACCAGCCTTCTATTT | SEQ ID NO: | 14 |
| Probe | TGCGATGCAGCTGAGACAACGTACG | SEQ ID NO: | 15 |

In Vitro Regulation of Transgene at the mRNA Level

To correlate the decrease in level of hGFP protein with mRNA depletion, the number of copies of hGFP mRNA was evaluated by QRT PCR with the RNA samples isolated from the same cells used for FACS analysis. At the mRNA level, the highest level was at 5 days after the infection in all the groups ($P<0.001$, FIG. 5A). The level of inhibition by dox at the mRNA level for all three vectors was similar to that of protein depletion (FIG. 5B). Background expression was lowest in cells infected with the preferred tet-off promoter system in rAAVS3, whereas cells infected with rAAVS2 had the highest degree of background expression. However, the degree of inhibition from rAAVS2 was a little lower at the RNA level than at the protein level, while the other two viruses had approximately the same level of inhibition at both the protein and RNA levels.

Evaluation of tTA Expression at the mRNA Level

The level of tTA gene product is one of the important factors contributing to the effectiveness of the tetracycline inducible system. Judging from the protein and mRNA assays of hGFP expression, the three vector designs appear to differ in degree of regulation. These differences may be caused by the distance between the two promoters in the constructs or by differences in the level of tTA. To address this, the entire tTA gene was sequenced in all four constructions and verified that no point mutations existed. Then, QRT-PCR was used to assay the mRNA level of tTA at three time points in cells grown in the presence or absence of dox. Similar to the hGFP mRNA level, all three vectors have the highest level of tTA mRNA level at 5 days treatment. The ratio of tTA copy number in "ON" versus "OFF" condition was 0.97 for rAAVS3, having the non-leaky tet-off promoter system, at 1 day, and 0.92 and 0.97 for 3 and 5 days, respectively. The ratio for rAAVS2 ranged from 0.93 at 3 days to 2.11 at 5 days, whereas that of rAAVS1 ranged from 2.34 at 3 days to 5.05 at 5 days. Therefore, the ratios of the level of tet expression in the "ON" and "OFF" states in these three viruses in which the tTA is driven by the CMV promoter are relatively stable ($P>0.05$ among the three tested time points).

In Vivo Regulation of Transgene Expression in Brain

Since the results from the in vitro studies showed that the rAAVS3 had the lowest background expression of transgene, the efficiency of regulation from this vector was studied in vivo in the CNS using rAAVS3hAADC and rAAVS3hGFP.

Animals Adult Fischer 344 rats (150-200 g) were obtained from Harlan (Indianapolis, Ind., USA), housed in the Children's Memorial Institute for Education and Research vivarium. Food and water were available ad libitum during a 12-h light/dark cycle and animals were treated according to institutional and NIH guidelines.

All surgical procedures were performed with the rats under isofluorane gas anesthesia using aseptic procedures. After a rat was anesthetized, it was placed in a Stoelting stereotaxic apparatus and 3 μl rAAVS3, having the non-leaky tet-off promoter system ($2\times10^{12}$ viral genome/ml) were injected into the striatum bilaterally. The coordinates were: AP: 1.0 mm, ML: 2.8/−2.8 mm and DV: −5.0 mm. After the skull was exposed, a burr hole was made with a dental drill above the injection site. The injection rate was 0.5 μl/min using a 10 μl syringe with 30 G needle (Hamilton, Reno, Nev., USA). The needle was retained for 5 min before being withdrawn at 1 mm/min. The skin and soft tissue were sutured and then the rats returned to the vivarium. For studies of regulation, three rats were provided with regular drinking water ("ON" group) and another three with water containing doxycycline (2 mg/ml) (Sigma, St. Louis, USA) ("OFF" group) right after surgery. After 4 weeks, rats were killed under anesthesia (213 mg chloral hydrate and 44 mg sodium pentobarbital per kilogram body weight i.p.). The brain was removed and cut in half sagittally. Transgene expression was studied in one striatum by histology and in the contralateral striatum by QRT-PCR.

The striatum of one hemisphere was quickly micro-dissected under a microscope (Wild M7A, Switzerland), frozen on dry ice, and then stored at −80° C. for real-time PCR. The other hemisphere was fixed by immersion in 4% paraformaldehyde with 5% sucrose in PBS, and cryoprotected by sequential immersion in 10, 20 and 30% sucrose in PBS. Frozen coronal sections (40 μm) were made of the striatum using a sliding microtome and stored in cryoprotective solution at −20° C.

The expression of the hrGFP was observed under epifluorescence. Determination of the number of hrGFP-positive cells in each injected striatum was carried out using Neurolcida™ software (Version 5.00, Williston, Vt., USA). Briefly, every sixth section of the striatum was mounted on a pre-cleaned microscope slide and cover-slipped with Fluor Save Reagent (Calbiochem, San Diego, Calif., USA). The region of interest (ROI), which containing most of positive cells, was first defined using a 4× objective and then the counting field was switched to a 40× objective. The meander scan mode was chosen to systematically move the section to each field within the counting regions and positive cells were marked. The summary of count from all sections was multiplied by 6 to estimate the total positive cells in each injection site. Sections through the injection site were also stained with H&E using standard methods.

Figure 6A:
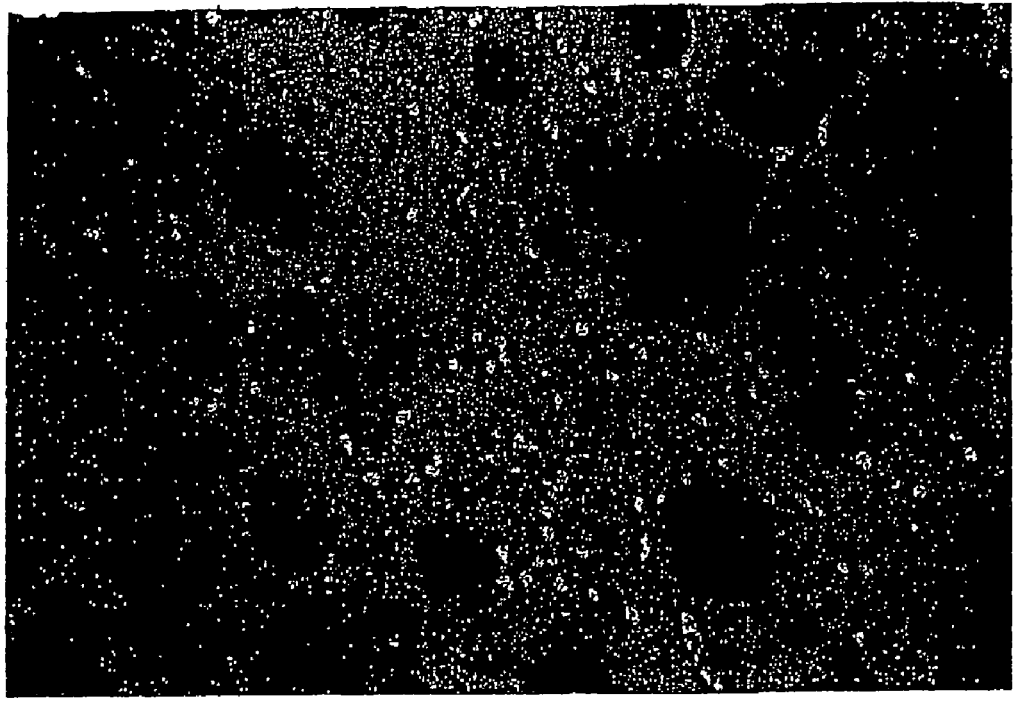
FIG. 6A shows expression of hGFP in rat striatum one month after injection with rAAVS3hGFP for rats maintained on regular drinking water, "ON"
Figure 6B:
FIG. 6B shows expression of hGFP in rat striatum one month after injection with rAAVS3hGFP for rats maintained on dox-containing water, "OFF"
Figure 6C:
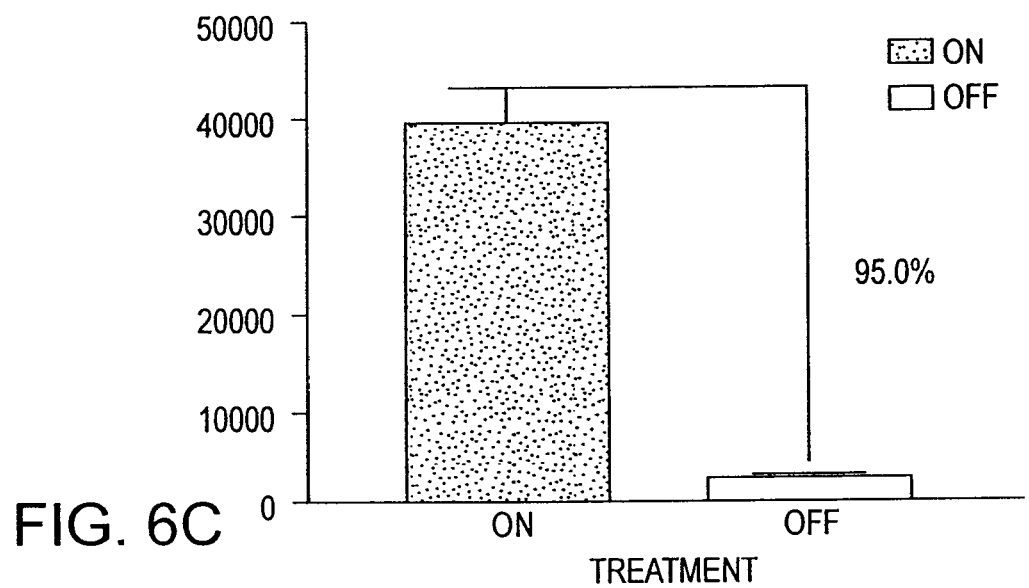
FIG. 6C shows cell counts of the hGFP-positive cells in injected rat striatum.
Figure 6D:
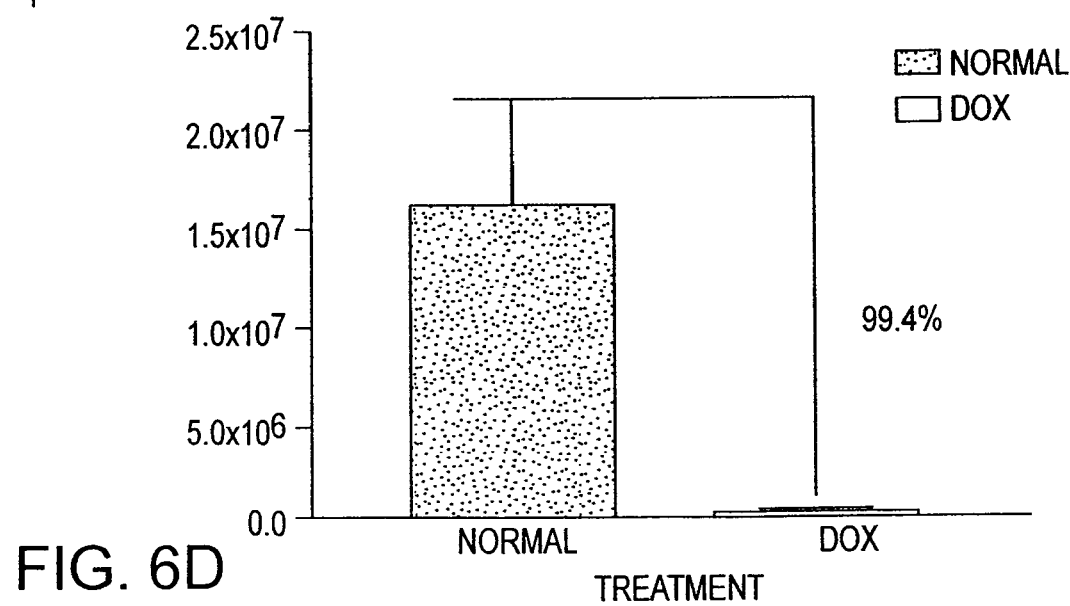
FIG. 6D shows the graphical representation of quantitation of hGFP mRNA in rat striatum by real-time RT-PCR.

Numerous positive cells with very bright fluorescence ($39546\pm6435$/striatum n=3) were observed in a widespread area of striatum of "ON" rats (FIG. 6A), whereas only rare bright positive cells ($2188\pm3363$/striatum) were observed in "OFF" rats (FIG. 6B). This is about 95% depression of transgene expression in terms of positive cell number. Meanwhile, no significant enrichment of inflammatory cells around injection sites could be found as evaluated by hematoxylin and eosin staining.

QRT-PCR analysis showed that there were $1.589\pm0.56\times10^7$ copies of hGFP per $10^4$ copies of β-actin in the "ON" group (n=3). In contrast only $9.9\pm0.57\times10^4$ copies of hGFP per $10^4$ copies of β-actin were found in the striata of "OFF" rats or less than 1% of the expression level in the absence of dox.

Figure 7A:
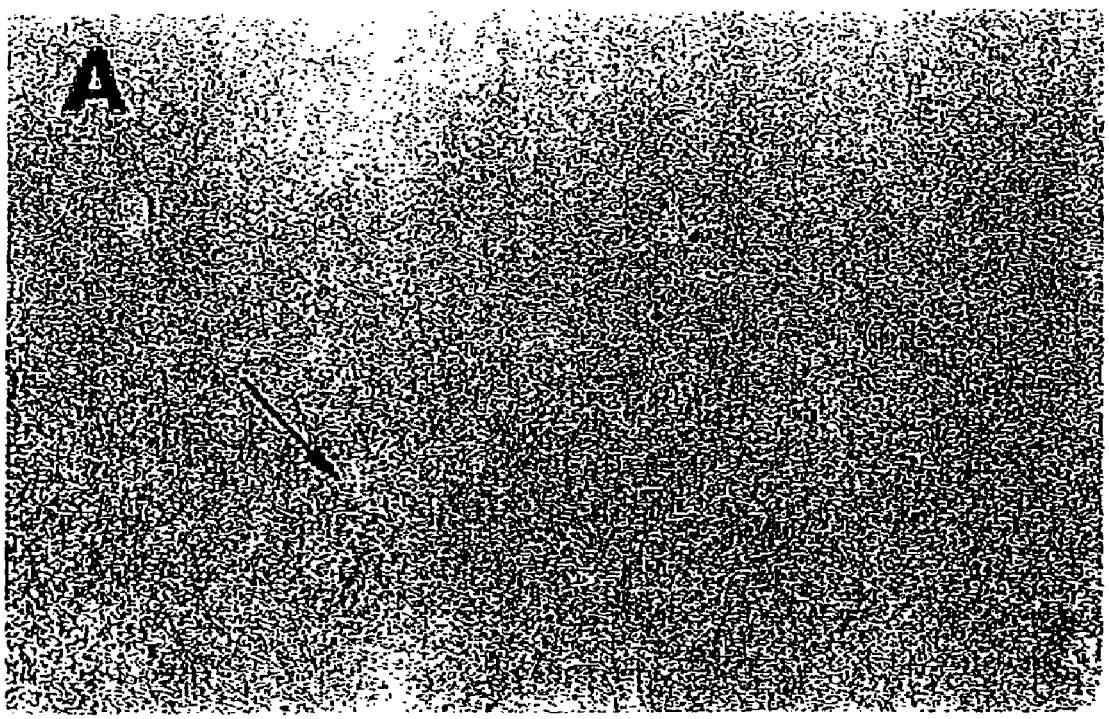
FIG. 7A shows expression of hAADC in rat striatum one month after injection with rAAVS3hAADC for rats maintained on dox-containing water, "OFF"
Figure 7B:
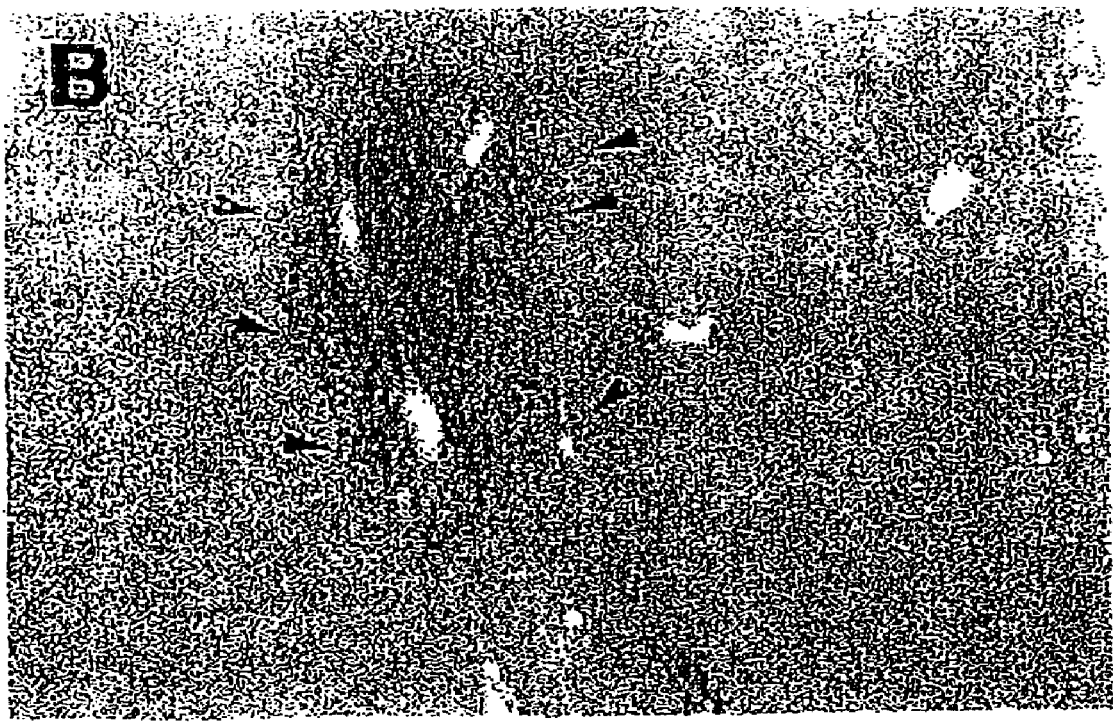
FIG. 7B shows expression of hAADC in rat striatum one month after injection with rAAVS3hAADC for rats maintained on regular drinking water, "ON"

Immunostaining of rat striatum showing hAADC expression is shown in FIGS. 7A and 7B. Rats were treated as described above. Rats received a 3 μl sterotaxic injection of rAAVSH3hAADC vector in the striatum and were maintained on either dox containing water (FIG. 7A) or regular water (FIG. 7B). At one month, rats were sacrificed and the striatae processed for immunoreactivity to hAADC. (See Sanchez-Pernaute, R. et al. *Mol. Ther.* 4: 324-330, 2001). Rat striatum showing needle track (arrow) for vector injection and absence of hAADC immunoreactive cells due to inhibition of transgene expression by dox is shown in FIG. 7A. Rat striatum showing numerous hAADC immunoreactive cells in the injection site in rats maintained on regular water is shown in FIG. 7B. hAADC expression may also be detected by western blotting and real time RT-PCR using standard techniques known to one of skill in the art.

Quantitative analysis of the expression of AADC mRNA and vector DNA will be achieved with the Real Time Quantitative RT-PCR & PCR 7700 System (Perkin-Elmer/Applied Biosystems, Inc.) as described above for hGFP.

Human GDNF Immunocytochemistry

Paraformaldehyde-fixed tissue sections will be incubated in 0.3% hydrogen peroxide for 15 min. Sections will be blocked for 60 min at room temperature in 3% normal goat serum (NGS) and 2% bovine serum albumin (BSA) in PBS containing 0.05% Triton-X100 (TX, Sigma). The sections will then be incubated overnight at room temperature in either a biotinylated polyclonal rabbit anti-GDNF antibody (R&D Systems) diluted 1:250 in 1% NGS, 1% BSA and 0.05% TX in PBS. The sections will then be incubated for 2.5 h at room temperature in a biotinylated goat anti-rabbit secondary antibody (Vector Laboratories, Burlingame, Calif.) diluted 1:500 in 1% NGS and 1% BSA in PBS. For immunocytochemical visualization, the sections will be incubated for 2 h in avidin-peroxidase conjugate (Vectastain ABC Elite, Vector Laboratories, Burlingame, Calif.) in PBS, followed by 2-3 min in 0.4 mg/mL diaminobenzidine (DAB), 0.8 mg/mL nickel sulfate, 0.005% $H_2O_2$ in 50 mM sodium acetate, 10 mM imidazol, pH=7.0. Between each step, sections will be washed several times in either PBS with 0.05% TX or PBS alone. (Connor, B. et al. *Gene Therapy*, 6: 1936-1951, 1999.)

Human GDNF ELISA

Figure 8:
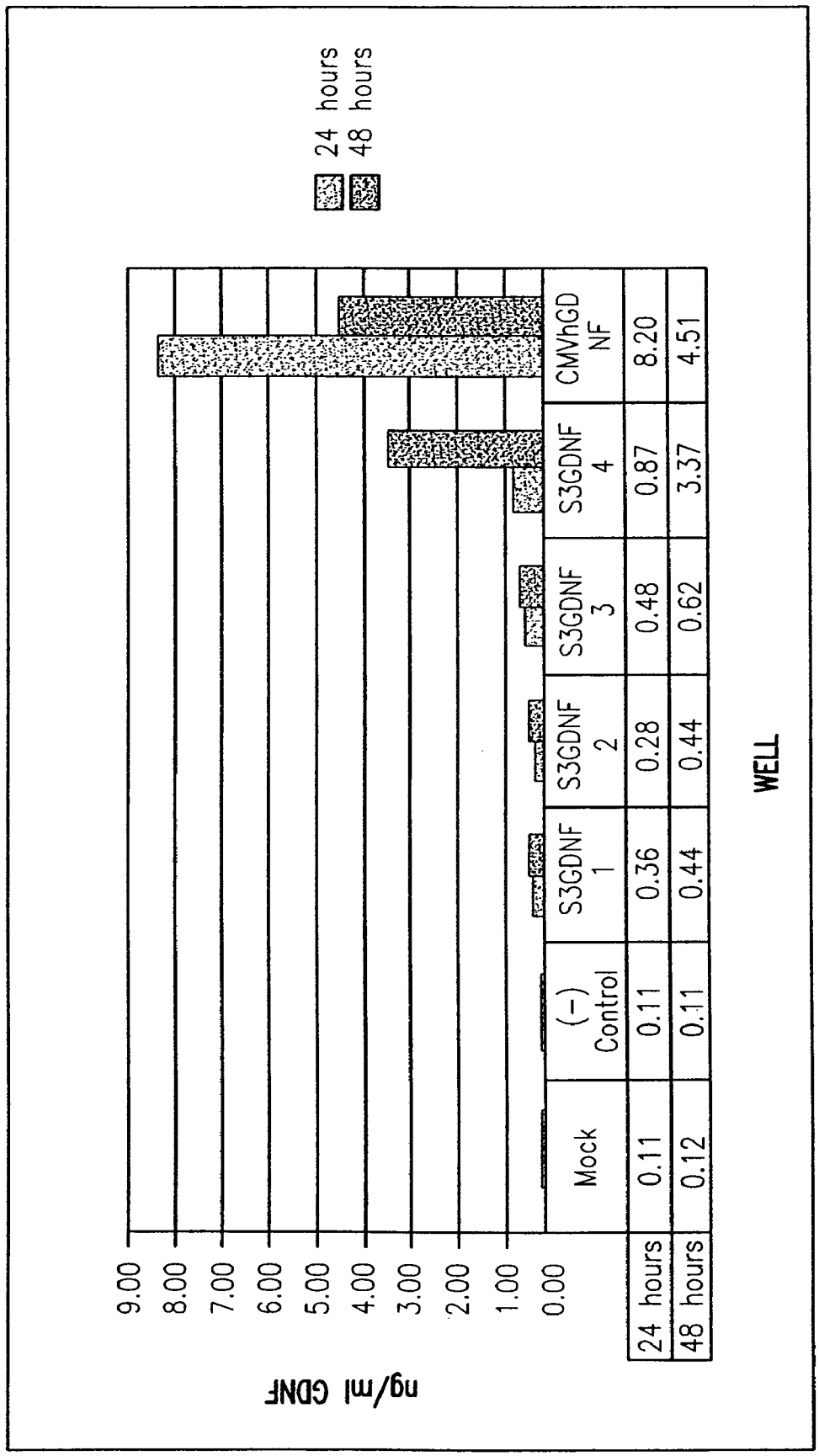
FIG. 8 shows GDNF levels in transfected U87MG cells.

Capture antibody (human monoclonal GDNF, 3 mg/ml; R & D Systems) was coated onto a 96-well plate overnight at 4° C. Wells were blocked with 1% BSA in PBS for 4 h at room temperature. The supernatant from the tissue samples (diluted 1:5) and serial dilutions of recombinant human GDNF protein (R & D Systems; 50 ml) was placed in the wells and incubated overnight at 4° C. Bound GDNF was detected using a polyclonal antibody to human GDNF (R & D Systems; 2 mg/ml) incubated overnight at 4° C. followed by a 4-h incubation in horseradish peroxidase-coupled secondary antibody (R & D Systems; 0.4 mg/ml). Visualization was with 0.02% ABTS and 0.03% $H_2O_2$ in 0.01 M sodium acetate buffer. Absorbance at 405 nm was measured using a Biolumin960 microassay reader (Molecular Dynamics). Quantitation of GDNF protein from the tissue culture samples was performed using a standard curve equation obtained from serial dilutions of recombinant human GDNF protein (R & D Systems). The amount of GDNF protein per milligram of tissue and per brain slice will also be tested and then be calculated similarly. (Choi-Lundberg, D. L. et al. *Science*, 275, 838-841, 1997.)

rAAVS3hGDNFkzk vectors were assayed in the GDNF ELISA. U87MG cells were transfected with the Kozak-like sequence containing plasmids according to standard transfection protocols. Supernatants were harvested at 24 and 48 hours post transfection and assayed in the GDNF ELISA. Results of the GDNF ELISA are shown in FIG. 8. In the transfection assays, the rAAVS3GDNF kzk4 plasmid increased expression of GDNF in the cells to the greatest extent. The Kozak-like sequences used in the plasmids are included in the forward primers used to clone each plasmid and the primers are shown below in Table 2.

Figure 9:
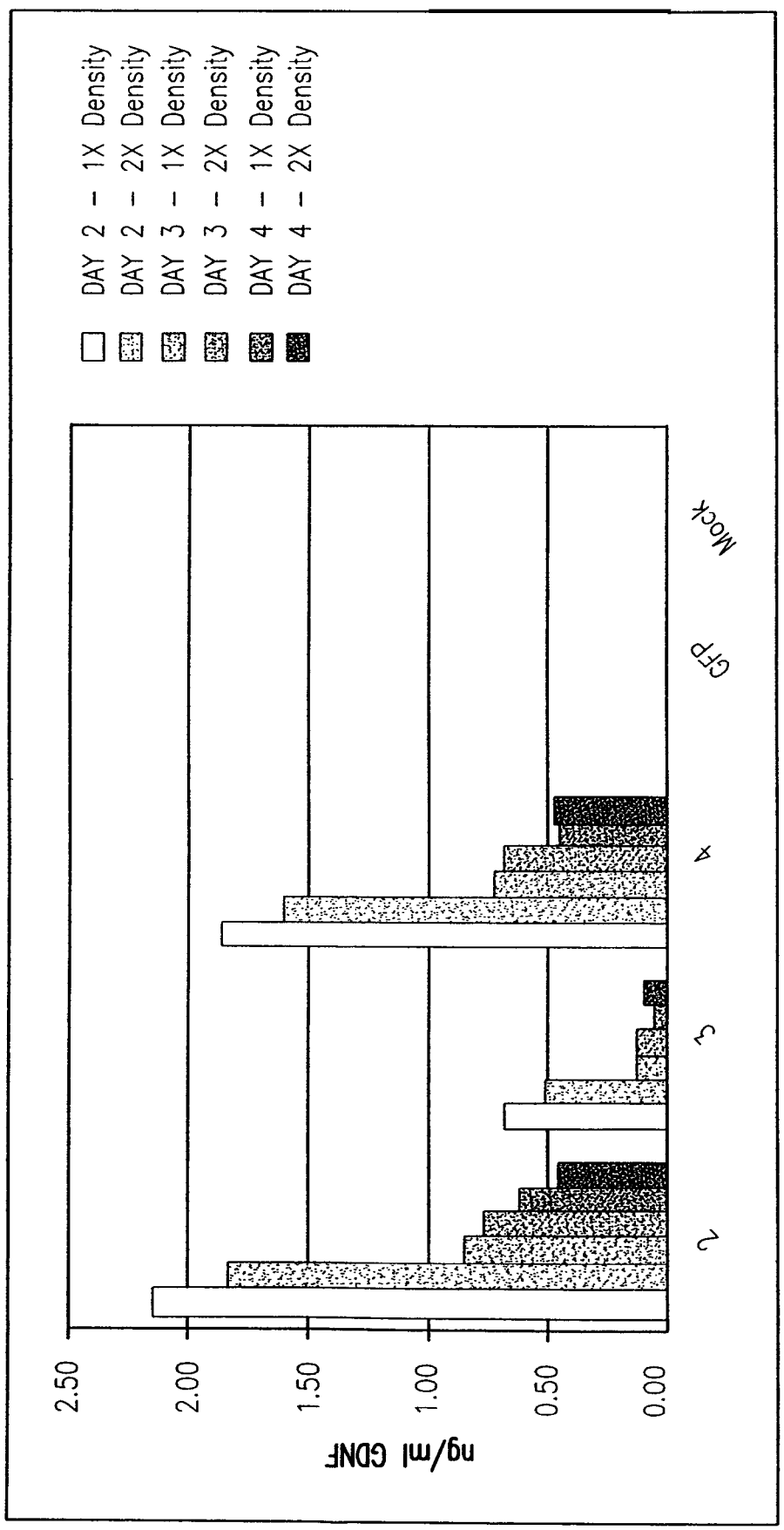
FIG. 9 shows GDNF levels in cells infected with rAAV virions.

The rAAVS3GDNFkzk constructs were also used to generate virions according to the protocols described above. U87MG cells were then infected with virions from each of the constructs and supernatants from the infected cells were assayed in the hGDNF ELISA. As shown in FIG. 9, rAAVS3hGDNFkzk2 and rAAVS3hGDNFkzk4 increased GDNF expression over controls at 2, 3 and 4 days after infection.

Figure 10:
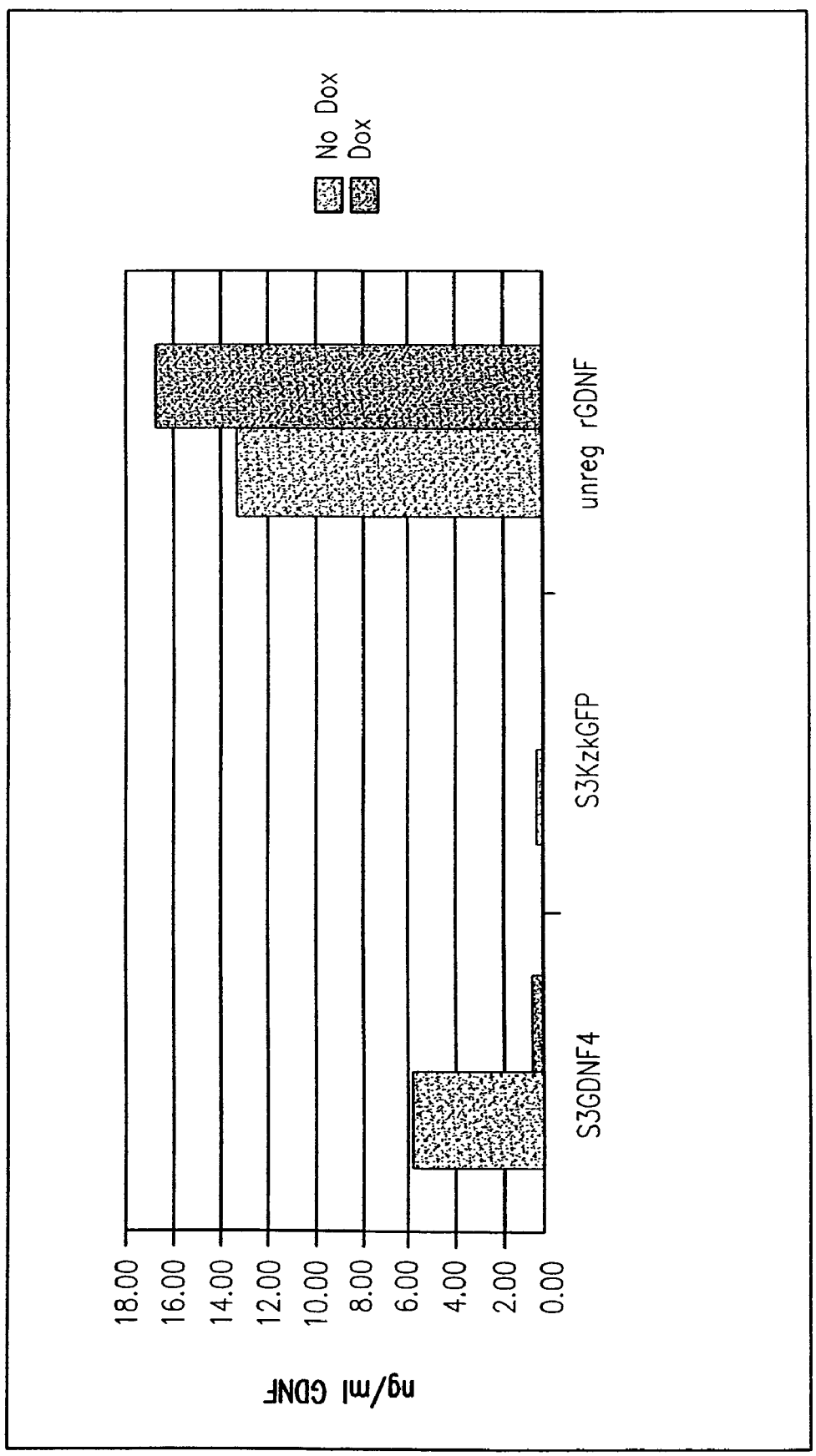
FIG. 10 shows regulation of GDNF levels by Dox.

A GDNF construct including a Kozak-like sequence was also assayed for responsiveness to Dox. rAAVS3hGDNFkzk4 virions were used to infect U87MG cells and the cells were treated with 2 ug/mlDox) or no Dox was added to the culture. Supernatants were harvested 3 days after infection and assayed in the GDNF ELISA. rAAVS3hGDNFkzk4 virions were also compared to both rAAVGFPkzk and a GDNF virion lacking a tetracycline regulatable promoter system. As shown in FIG. 10, the rAAVS3hGDNFkzk4 construct increased GDNF expression and was regulatable by Dox.

TABLE 2

| | | | |
|---|---|---|---|
| kzk1 Forward Primer | rAAVS3hGDNFkzk1 GCGGCCGCATGAAGTTATGGGATGTCGT | | SEQ ID NO: 16 |
| Reverse Primer | AATTGCGGCCGCTCAGATACATCCACACCTTT | | SEQ ID NO: 17 |

TABLE 2-continued

| | | | |
|---|---|---|---|
| kzk2 Forward Primer | rAAVS3hGDNFkzk2 AATTATCGATGGGTGGGTCTGCGGAGACCCGA | | SEQ ID NO: 18 |
| Reverse Primer | Same as kzk1 | | SEQ ID NO: 17 |
| kzk3 Forward Primer | rAAVS3hGDNFkzk3 AATTATCGATGCCGGACGGGACTTTCA | | SEQ ID NO: 19 |
| Reverse Primer | Same as kzk1 | | SEQ ID NO: 17 |
| kzk4 Forward Primer | rAAVS3hGDNFkzk4 GATATCGATATCGCCGCCACCATGAAGTTATGGGA | | SEQ ID NO: 20 |
| Reverse Primer | Same as kzk1 | | SEQ ID NO: 17 |
| Forward Primer | hGDNF internal sequence CTTCGCGCTGAGCAGTGACT | | SEQ ID NO: 21 |
| Reverse Primer | AGTCACTGCTCAGCGCGAAG | | SEQ ID NO: 22 |
| GFP Forward Primer | rAAVS3rGFPkzk GATATCGATATCGCCGCCACCATGGTGAGCAAGCAGA | | SEQ ID NO: 23 |
| Reverse Primer | GCCGCGCGGCCGCTCACACCCACTCGTGCA | | SEQ ID NO: 24 |

In Vivo PET Imaging of Nucleic Acid Expression

A direct positron emission tomography (PET) image will be used to determine expression and a therapeutic effect of the expression of a therapeutic protein in a patient or an animal model having a nervous system disorder. A rAAVS3 vector having a nucleic acid encoding protein that provide a therapeutic effect on a patient or animal having a nervous system disorder will be administered to a patient or animal model as discussed above. A labeled tracer will also be administered to indicate activity and location of the therapeutic protein encoded by the nucleic acid.

rAAVS3AADC will be administered to a patient or animal model having a nervous system disorder. PET imaging will be used to monitor uptake of an AADC tracer, 6-[$^{18}$F] fluoro-L-m-tyrosine (FMT). The FMT will indicate the activity of the ADCC protein from the rAAVS3AADC virions and the location of the ADCC protein within the nervous system. PET scans will be performed using a Siemens-CTI ECAT EXACT (Model 31) 31-slice scanner following administration of the rAAVS3AADC virions. The PET data will be analyzed by determining the radioactivity counts for the striatum and the cerebellum and creating radioactivity count ratios using the cerebellum as a reference region because FMT uptake is negligible and should not change between baseline and post treatment studies. Change scores for the count ratios will be calculated representing the percentage change from baseline to post administration of the virions. The ratio method will require emission acquisition times of only 30 minutes and will be advantageous for use with patients.

The PET imaging will also be used to evaluate the leakiness of the rAAVS3AADC as described above. PET imaging will be used to evaluate both the "ON" state after delivery of the rAAVS3AADC virions to the cells of a patient having a nervous system disorder and the "OFF" state wherein tetracycline or doxycycline has been administered to regulate the expression of the protein encoded by the first nucleic acid. Radioactivity count ratios for the "ON" and the "OFF" states will be compared to evaluate the regulation of the expression by tetracycline or doxycycline.

An animal model for PET imaging studies will also be used to evaluate the expression and therapeutic effect of rAAVS3AADC virions on a nervous system disorder. Parkinsonian monkeys will be used having lesions created by 1-methyl-4-phenyl-1,2,3,6-tetrahydropyridine (MPTP)-HCl infused unilaterally into an intracarotid artery to create near-complete lesions on the side of the infusion and mild to moderate damage in the other hemisphere. rAAVS3AADC virions and FMT will be administered after the MPTP lesions are created. PET imaging will be performed as described above. Additional animal models, such as aged (20 month) rats will be used with PET imaging to monitor the therapeutic effect and the leakiness of the proteins encoded by the first nucleic acid delivered to the nervous system. (See Eberling, J. L., *Mol. Ther.*, 8:873-875, 2003.)

PET image evaluation will be combined with evaluation of clinical symptoms in patients having a nervous system disorder to evaluate the amelioration of the clinical symptoms. In patients having a nervous system disorder, for example Parkinson's Disease, the clinical symptoms will include bradykinesia, rigidity and resting tremor. For the animal models having a nervous system disorder, the physical symptoms are discussed below.

Method of Assaying a Therapeutic Effect on a Nervous System Disorder

An animal model in which the animal exhibits a phenotype consistent with a nervous system disorder will be used for assaying a therapeutic effect of delivery of a rAAVS3 vector. Aged rats (20 months) or 60 day old rats with progressive 6-OHDA lesions of the nigrostriatal projection will be used for rAAVS3GDNF delivery assessment. (See Connor, B., *Gene Ther.*, 6: 1936-1951, 1999; Choi-Lundberg, D. L. et al. *Science*, 275, 838-841, 1997.)

In animals with a unilateral lesion of the nigrostriatal dopaminergic (DA) system, the injection of drugs that act to release dopamine, such as amphetamine, will induce rotational behavior towards the denervated striatum. Animals will turn away from the hemisphere where there is greater amphetamine-stimulated dopamine release and greater dopamine receptor stimulation. Animals will be injected with rAAVS3GDNF, or rAAVS3GFP, or no vector treatment.

Amphetamine-induced rotational activity will be recorded for 60 min following an i.p. injection of 5 mg DL-amphetamine per kg body weight. Rats will be placed in a plastic bowl (depth 18 cm; diameter 38 cm) and video taped and rated. Base line amphetamine rotation tests will be performed 7 days before the 6-OHDA lesions and the results will be used to assign the side of the subsequent 6-OHDA lesion. Rats exhibiting net clockwise turns will be lesioned in the left striatum, while rats exhibiting net counter-clockwise turns will be lesioned in the right striatum. Following the 6-OHDA lesion, amphetamine-induced rotational behavior will be tested 14 and 35 days after lesioning.

The number of clockwise and counter-clockwise turns will be counted and expressed as the number of net rotations per minute to the lesioned (ipsilateral) hemisphere (net rotations per minute to ipsilateral hemisphere=ipsilateral rotations-contralateral rotations/time). Repeated-factor, two-way ANOVA will be performed to evaluate the rotational behavior. Rotational behavior will be evaluated pre-lesioning with 6-OHDA, and post lesioning, and with and without administration of the rAAVS3GDNF. A decrease in the ipsilateral rotational behavior when compared with control groups will indicate a therapeutic effect of the administration of the rAAVS3GDNF.

Spontaneous exploratory forelimb use will also be used to evaluate the therapeutic effect of the rAAVS3GDNF on the animal model. The spontaneous exploratory forelimb use test is a non-drug-induced test of forelimb locomotor function which has been shown to correlate with DA depletion in the lesioned hemisphere. Following a unilateral 6-OHDA lesion of the nigrostriatal system, rats preferentially use the forelimb ipsilateral to the side of the lesion to initiate and terminate weight shifting movements during rearing and exploration along vertical surfaces.

Rats will be videotaped for 5 minutes in a Plexiglas® chamber before and 7, 14, 21, and 28 days after 6-OHDA lesioning. Spontaneous exploratory forelimb use will be scored using forelimb asymmetry analysis. The number of ipsilateral, contralateral and both paw placements performed against the chamber wall during vertical/lateral explorations and the paw used to land following exploration will be quantified during slow-motion playback of the videotaped session. The results will be presented as percent of total ipsilateral forelimb use by first calculating the percentage of ipsilateral wall (ipsilateral wall placement/ipsilateral wall+contralateral wall+both wall placement×100) and ipsilateral land (ipsilateral land placement/ipsilateral land+contralateral land+both land placement×100) movements. The percentage of ipsilateral wall and ipsilateral land placements will then be added together and divided by two. The calculation will assure that the wall and land movements will be weighted evenly and will result in a measure of ipsilateral forelimb use relative to total forelimb movement. Rats that exhibit less than five forelimb placements during the 5 minutes will be removed from analysis. One-way ANOVA will be used to analyze the preferential use of the ipsilateral forelimb post 6-OHDA lesioning compared with control groups. A decrease in the preferential use of the ipsilateral forelimb when compared with control groups will indicate a therapeutic effect of the administration of the rAAVS3GDNF.

An animal model exhibiting a nervous system disorder phenotype may also be used to examine the therapeutic effect of rAAVS3hAADC. Apomorphine-induced lesions in rat striatum may be used in combination with rotational behavior to evaluate the therapeutic effect of rAAVS3hAADC administration. Rotational behavior will be evaluated as discussed above. (See also Sánchez-Perante et al., *Mol. Ther.* 4(4): 324-330, 2001.)

Abbreviated in Vivo Protocol for rAAVS3hGDNF Testing

The tet-regulated hGDNF vector, rAAVS3hGDNF was tested for efficacy in the progressive 6-OHDA lesion model of Parkinson's disease. Before virus injection surgery, baseline behavioral data were collected on all animals. Rats were injected with DL-amphetamine (5 mg/kg i.p.) and tested for rotational behavior over one hour. Animals were divided evenly among the groups for equal rotation per group and the hemisphere for virus injection/6-OHDA lesion was assigned. Rats with an intrinsic clockwise (R) bias were lesioned in the left striatum and those with a counter-clockwise (L) intrinsic bias were lesioned in the right striatum. All rats were injected bilaterally with fluorogold (FG (0.2 µl, 2% FG in 0.9% saline) at coordinates: 0 A/P, −/+2.5 M/L, −5 D/V to allow for quantitation of striatal-projecting dopamine neurons cells that survive in the substantia nigra after treatment and lesioning. Animals were injected with the rAAV-S3hGDNF or the rAAV-hrS3GFP control virus or saline unilaterally at the FG injection site and at two more striatal sites in the pre-determined hemisphere with 2 µl virus or saline injected at each site. The viral titers used were rAAV-S3 hrGFP—$2.84 \times 10^{12}$ vector genomes (vg)/ml and rAAV-S3hGDNF—$7.21 \times 10^{13}$ vg/ml—diluted to $5 \times 10^{13}$ vg/ml for use.

One week after viral injection rats were lesioned using 2.8 µl of 5 mg 6-OHDA dissolved in 592 µl of 0.2 mg/ml ascorbic acid in 0.9% sterile saline injected into striatum on the hemisphere previously assigned (same as virus) in the same stereotactic position as the FG injection. Two and four weeks after lesioning rats were tested for amphetamine rotation as previously described.

On the final day of the experiment (four weeks after lesion) rats were injected with amphetamine and tested for rotational behavior 2 hrs prior to perfusion. All rats were sacrificed as appropriate for their assigned group. 5 rats from each group were transcardially perfused with ice-cold saline and immediately the striatum and cerebellum were dissected. Tissue was flash frozen for biochemical studies. Both the virus injected (ipsilateral) and non-injected (contralateral) sides of the striatum were collected and processed. Protein was extracted from these samples for ELISA assay to quantify the amount of GDNF present in each. 5 or 6 rats from each group were transcardially perfused with 4% paraformaldehyde and processed for immunohistochemistry. Both the striatum and substantia nigra were sectioned at 40 µM.

Figure 12:
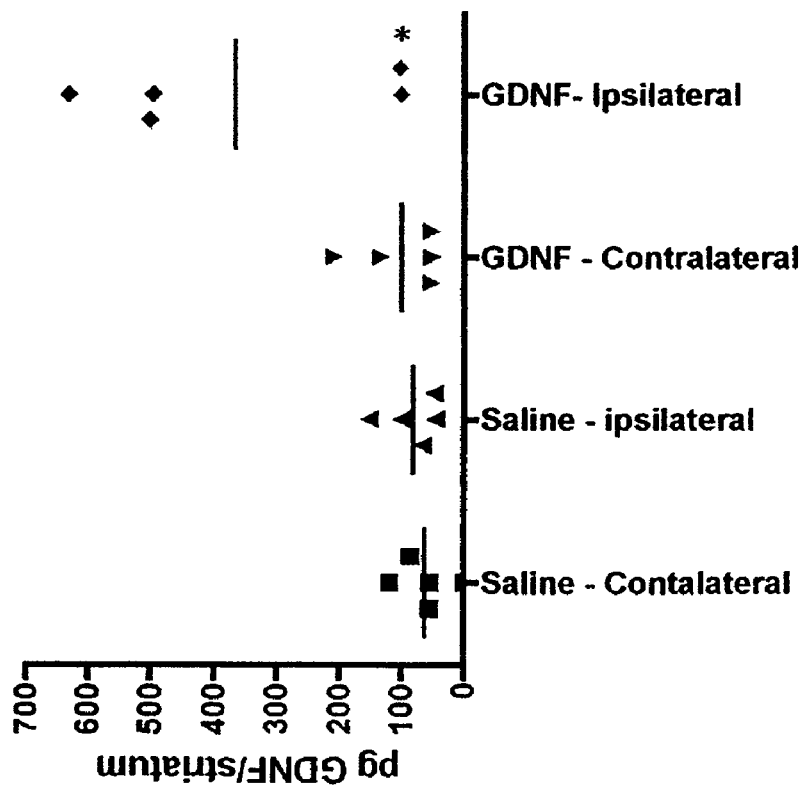
FIG. 12 shows GDNF protein levels in treated and untreated brain tissue.
Figure 11:
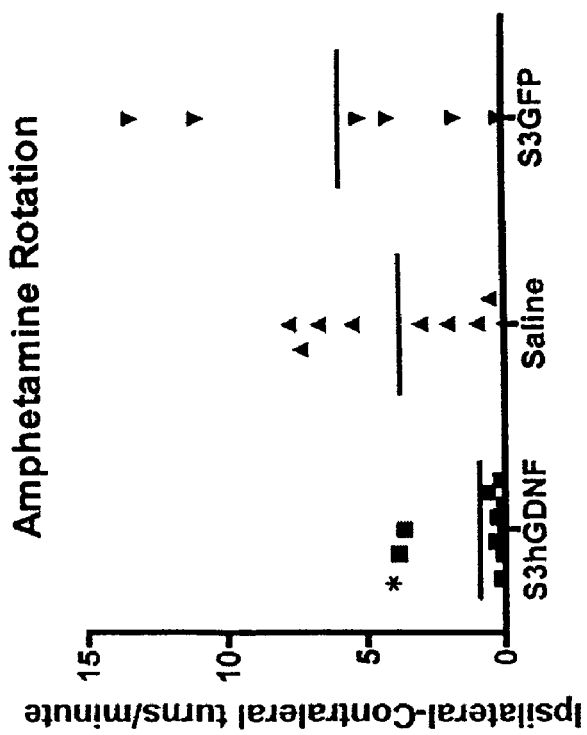
FIG. 11 shows amphetamine rotational behavior in rats injected with rAAVS3hGDNF or controls.

Results of the amphetamine rotational testing and GDNF ELISA are shown in FIGS. 11 and 12, respectively. As shown in FIG. 11, rats injected with the rAAVS3hGDNF vector had significantly lower levels of amphetamine-induced rotation than rats injected with the control rAAVS3rhGFP vector or saline. Rats showing behavioral improvement also had high levels of hGDNF protein in the striatum as shown in FIG. 12. Two rats which did not have high levels of hGDNF protein in the striatum also did not display behavioral improvement and most likely did not receive vector due to technical reasons (Indicated by * in FIGS. 11 and 12).

Although the invention herein has been described in connection with a preferred embodiment thereof, it will be appreciated by those skilled in the art that additions, modifications, substitutions, and deletions not specifically described may be made without departing from the spirit and scope of the invention as defined in the appended claims. It is therefore intended that the foregoing detailed description be regarded as illustrative rather than limiting, and that it be understood that it is the following claims, including all equivalents, that are intended to define the spirit and scope of this invention.

The invention claimed is:

1. A method of delivering a first nucleic acid to a nervous system cell in a patient with a nervous system disorder, the method comprising:
   providing a recombinant adeno-associated viral (rAAV) vector, the vector comprising:
      SEQ ID NO: 20 operably linked to a first nucleic acid encoding a protein that provides a therapeutic effect on the nervous system disorder;
      a second nucleic acid encoding a tetracycline-controlled transactivator;
      inverted terminal repeats of AAV; and
      a tetracycline-off regulatable promoter system comprising a first promoter operably linked to the first nucleic acid and a second promoter operably linked to the second nucleic acid, wherein the first and second promoters drive expression in opposite directions in the vector, towards each other and away from the inverted terminal repeats, and wherein expression of a product from the first nucleic acid is regulatable by the promoter system; and
   administering the rAAV vector to the nervous system cell.

2. The method of claim 1, further comprising providing a Kozak-like sequence operably linked to the first nucleic acid.

3. The method of claim 1, further comprising providing a tetracycline response element operably linked to the first promoter.

4. The method of claim 1, wherein the first nucleic acid comprises glial cell line-derived neurotrophic factor (GDNF), and other members of the GDNF family including neurturin, persephin and artemin, aromatic amino-acid decarboxylase, brain-derived neurotrophic factor, nerve growth factor, neurotrophin (NT)-3, NT-4, BMP4, ciliary neurotrophic factor, platelet-derived neurotrophic factor, leukemia inhibitory factor, interleukins, tyrosine hydroxylase, dopamine-β-hydroxylase, phenylethanolamine N-methyltransferase, tryptophan hydroxylase, vesicular monoamine transporter, dopamine transporter, catecholamine, serotonin and glutamate transporters, vascular endothelial growth factor, superoxide dismutase, catalase, glutathione peroxidase, adenosine A-1 receptor, glutamate decarboxylase, choline acetyltransferase, cholinergic nicotinic or muscarinic receptors, neuropeptides, including enkephalin, dynorphin, substance P, neuropeptide Y, GABA-A receptor isoforms, calcium-dependent potassium channels, ATP-sensitive potassium channels, bcl2, $bcl_{xl}$, and bax, caspase, dominant-negative nucleic acids against caspase enzymes, and tumor necrosis related apoptosis-inducing factor, nogo, netrins, semaphorins, N-CAM, eph receptors, eph ligands, sonic hedgehog, nurr-1, HOX genes, LIM genes, POU genes, c-fos, or fosB.

5. The method of claim 1, wherein the first nucleic acid comprises glial cell line-derived neurotrophic factor or aromatic amino acid decarboxylase.

6. The method of claim 1, wherein the first promoter comprises a cytomegalovirus promoter.

7. The method of claim 1, wherein the second promoter comprises a cytomegalovirus promoter.

8. The method of claim 1, further comprising making rAAV virions for administering the rAAV vector to the nervous system cell.

9. The method of claim 1, wherein administering the rAAV vector comprises administering the rAAV vector into a brain of a mammal.

10. The method of claim 1, further comprising administering tetracycline or doxycycline to regulate the expression.

11. The method of claim 10 wherein administering tetracycline or doxycycline "OFF" regulates the expression to about 5% or less compared to the expression without tetracycline or doxycycline.

12. The method of claim 10 wherein administering tetracycline or doxycycline "OFF" regulates the expression to about 1% or less compared to the expression without tetracycline or doxycycline.

13. The method of claim 1, wherein the nervous system disorder is Parkinson's Disease.

* * * * *

```
                       SEQUENCE LISTING

<160> NUMBER OF SEQ ID NOS: 25

<210> SEQ ID NO 1
<211> LENGTH: 22
<212> TYPE: DNA
<213> ORGANISM: Artificial
<220> FEATURE:
<223> OTHER INFORMATION: GFP forward primer

<400> SEQUENCE: 1
acctgatcga ggagatgttc gt                                              22

<210> SEQ ID NO 2
<211> LENGTH: 20
<212> TYPE: DNA
<213> ORGANISM: Artificial
<220> FEATURE:
<223> OTHER INFORMATION: GFP reverse primer

<400> SEQUENCE: 2
aggccggtga tggtcttctt                                                 20

<210> SEQ ID NO 3
<211> LENGTH: 22
<212> TYPE: DNA
<213> ORGANISM: Artificial
<220> FEATURE:
<223> OTHER INFORMATION: GFP probe

<400> SEQUENCE: 3
caagggccgc aacttcccca ac                                              22
```

<210> SEQ ID NO 4
<211> LENGTH: 19
<212> TYPE: DNA
<213> ORGANISM: Artificial
<220> FEATURE:
<223> OTHER INFORMATION: TA forward primer

<400> SEQUENCE: 4
tcgacgcctt agccattga                                           19

<210> SEQ ID NO 5
<211> LENGTH: 24
<212> TYPE: DNA
<213> ORGANISM: Artificial
<220> FEATURE:
<223> OTHER INFORMATION: TA reverse primer

<400> SEQUENCE: 5
tcgcgatgac ttagtaaagc acat                                     24

<210> SEQ ID NO 6
<211> LENGTH: 36
<212> TYPE: DNA
<213> ORGANISM: Artificial
<220> FEATURE:
<223> OTHER INFORMATION: TA probe

<400> SEQUENCE: 6
agaataggca ccatactcac ttttgccctt tagaag                        36

<210> SEQ ID NO 7
<211> LENGTH: 25
<212> TYPE: DNA
<213> ORGANISM: Artificial
<220> FEATURE:
<223> OTHER INFORMATION: Beta Actin Forward Primer

<400> SEQUENCE: 7
tcacccacac tgtgcccatc tacga                                    25

<210> SEQ ID NO 8
<211> LENGTH: 25
<212> TYPE: DNA
<213> ORGANISM: Artificial
<220> FEATURE:
<223> OTHER INFORMATION: Beta Actin Reverse Primer

<400> SEQUENCE: 8
cagcggaacc gctcattgcc aatgg                                    25

<210> SEQ ID NO 9
<211> LENGTH: 26
<212> TYPE: DNA
<213> ORGANISM: Artificial
<220> FEATURE:
<223> OTHER INFORMATION: Beta Actin Probe

<400> SEQUENCE: 9
atgccctccc ccatgccatc ctgcgt                                   26

<210> SEQ ID NO 10
<211> LENGTH: 20
<212> TYPE: DNA
<213> ORGANISM: Artificial
<220> FEATURE:
<223> OTHER INFORMATION: AADC Forward Primer

```
<400> SEQUENCE: 10
gcaggcagtg cattcatctg                                              20

<210> SEQ ID NO 11
<211> LENGTH: 24
<212> TYPE: DNA
<213> ORGANISM: Artificial
<220> FEATURE:
<223> OTHER INFORMATION: AADC Reverse Primer

<400> SEQUENCE: 11
cagtcaaaat tcaccaatag ccat                                         24

<210> SEQ ID NO 12
<211> LENGTH: 26
<212> TYPE: DNA
<213> ORGANISM: Artificial
<220> FEATURE:
<223> OTHER INFORMATION: AADC Probe

<400> SEQUENCE: 12
ctgagttccg gcaccttctg aatgga                                       26

<210> SEQ ID NO 13
<211> LENGTH: 21
<212> TYPE: DNA
<213> ORGANISM: Artificial
<220> FEATURE:
<223> OTHER INFORMATION: GDNF Forward Primer

<400> SEQUENCE: 13
ctgacttggg tctgggctat g                                            21

<210> SEQ ID NO 14
<211> LENGTH: 24
<212> TYPE: DNA
<213> ORGANISM: Artificial
<220> FEATURE:
<223> OTHER INFORMATION: GDNF Reverse Primer

<400> SEQUENCE: 14
ttgtcactca ccagccttct attt                                         24

<210> SEQ ID NO 15
<211> LENGTH: 25
<212> TYPE: DNA
<213> ORGANISM: Artificial
<220> FEATURE:
<223> OTHER INFORMATION: GDNF Probe

<400> SEQUENCE: 15
tgcgatgcag ctgagacaac gtacg                                        25

<210> SEQ ID NO 16
<211> LENGTH: 28
<212> TYPE: DNA
<213> ORGANISM: Artificial
<220> FEATURE:
<223> OTHER INFORMATION: kzk1 forward primer

<400> SEQUENCE: 16
gcggccgcat gaagttatgg gatgtcgt                                     28

<210> SEQ ID NO 17
```

```
<211> LENGTH: 32
<212> TYPE: DNA
<213> ORGANISM: Artificial
<220> FEATURE:
<223> OTHER INFORMATION: kzk Reverse Primer

<400> SEQUENCE: 17
aattgcggcc gctcagatac atccacacct tt                              32

<210> SEQ ID NO 18
<211> LENGTH: 32
<212> TYPE: DNA
<213> ORGANISM: Artificial
<220> FEATURE:
<223> OTHER INFORMATION: kzk2 Forward Primer

<400> SEQUENCE: 18
aattatcgat gggtgggtct gcggagaccc ga                              32

<210> SEQ ID NO 19
<211> LENGTH: 27
<212> TYPE: DNA
<213> ORGANISM: Artificial
<220> FEATURE:
<223> OTHER INFORMATION: kzk3 Forward primer

<400> SEQUENCE: 19
aattatcgat gccggacggg actttca                                    27

<210> SEQ ID NO 20
<211> LENGTH: 35
<212> TYPE: DNA
<213> ORGANISM: Artificial
<220> FEATURE:
<223> OTHER INFORMATION: kzk4 Forward Primer

<400> SEQUENCE: 20
gatatcgata tcgccgccac catgaagtta tggga                           35

<210> SEQ ID NO 21
<211> LENGTH: 20
<212> TYPE: DNA
<213> ORGANISM: Artificial
<220> FEATURE:
<223> OTHER INFORMATION: GDNF internal sequence forward primer

<400> SEQUENCE: 21
cttcgcgctg agcagtgact                                            20

<210> SEQ ID NO 22
<211> LENGTH: 20
<212> TYPE: DNA
<213> ORGANISM: Artificial
<220> FEATURE:
<223> OTHER INFORMATION: GDNF internal sequence reverse primer

<400> SEQUENCE: 22
agtcactgct cagcgcgaag                                            20

<210> SEQ ID NO 23
<211> LENGTH: 37
<212> TYPE: DNA
<213> ORGANISM: Artificial
<220> FEATURE:
<223> OTHER INFORMATION: GFPkzk forward primer

<400> SEQUENCE: 23
```

```
gatatcgata tcgccgccac catggtgagc aagcaga                                37

<210> SEQ ID NO 24
<211> LENGTH: 30
<212> TYPE: DNA
<213> ORGANISM: Artificial
<220> FEATURE:
<223> OTHER INFORMATION: GFPkzk reverse primer

<400> SEQUENCE: 24
gccgcgcggc cgctcacacc cactcgtgca                                        30

<210> SEQ ID NO 25
<211> LENGTH: 10
<212> TYPE: DNA
<213> ORGANISM: artificial
<220> FEATURE:
<223> OTHER INFORMATION: Kozak-like sequence
<220> FEATURE:
<221> NAME/KEY: misc_feature
<222> LOCATION: (4)..(4)
<223> OTHER INFORMATION: R may be A or G

<400> SEQUENCE: 25 gccrccatgg                                                              10
```